(12) United States Patent
Sharon et al.

(10) Patent No.: US 7,727,183 B2
(45) Date of Patent: Jun. 1, 2010

(54) SYRINGE ASSEMBLY

(76) Inventors: Igal Sharon, 5 Hadar St, Caesaria (IL) 38900; Yohanan Maggeni, Ilania (IL) 15255

( * ) Notice: Subject to any disclaimer, the term of this patent is extended or adjusted under 35 U.S.C. 154(b) by 422 days.

(21) Appl. No.: 11/618,938

(22) Filed: Jan. 2, 2007

(65) Prior Publication Data
US 2008/0082044 A1 Apr. 3, 2008

(51) Int. Cl.
*A61M 37/00* (2006.01)
(52) U.S. Cl. ..................................... 604/89
(58) Field of Classification Search ............ 604/89
See application file for complete search history.

(56) References Cited

U.S. PATENT DOCUMENTS

| | | | |
|---|---|---|---|
| 4,159,570 A | | 7/1979 | Baskas |
| 5,281,198 A | * | 1/1994 | Haber et al. .............. 604/86 |
| 5,489,267 A | | 2/1996 | Moreno |
| 6,616,627 B2 | | 9/2003 | Willis |
| 6,743,194 B2 | | 6/2004 | Sharon |

\* cited by examiner

*Primary Examiner*—Nicholas D Lucchesi
*Assistant Examiner*—Jason Flick
(74) *Attorney, Agent, or Firm*—Deborah Gador

(57) ABSTRACT

A syringe assembly consists of two basic types of assembly units: a dispensing unit, and a separate, independent plunger unit. The dispensing unit and the plunger unit are assembled together coaxially to form a two-unit syringe assembly for storage or prior to use. At least the dispensing unit is a container for a material to be dispensed and, by inserting one or more extension units between the dispensing unit and the plunger unit, additional compartments may be added. Each extension unit may contain a different component of a formulation in any predetermined quantity. The syringe assembly allows the user to store one or more components of a formulation in separate individual units that can be assembled easily into a single multi-compartment syringe assembly, which can store the multiple components separately until they are ready for use, at which time the components may be mixed to form the formulation.

18 Claims, 19 Drawing Sheets

SYRINGE ASSEMBLY

FIELD OF THE INVENTION

This invention relates to syringe assembly systems in general and, in particular, to multi-unit syringe assemblies for separately storing each of one or more components of a formulation in separate containers until ready for dispensing or mixing prior to dispensing.

BACKGROUND OF THE INVENTION

A multi-compartment syringe, allowing the user to store multiple components of a medicament in separate, individually sealed compartments until ready for use is known in the art. A multi-compartment syringe comprising a single multi-compartment barrel, is disclosed in U.S. Pat. No. 6,743,194, herein "the '194 patent", which is assigned to the assignee of the present application and whose contents are incorporated by reference. In the '194 patent, the syringe is a single barreled syringe that may be configured to store two or more components of a medicament or other formulation separately in hermetically sealed compartments until just prior to use. When ready to mix the contents of the pre-filled syringe, the seal(s) partitioning the compartments can be easily unsealed, establishing a two-way flow communication between the compartments so that the contents of each compartment can be mixed to form the medicament.

Thus, the '194 patent describes and claims a syringe including a syringe body having an opening at each of its top and bottom ends; a shoulder provided between the top and the bottom ends defining a top-compartment sidewall portion between the top end and the shoulder; the shoulder further defining a bottom-compartment sidewall portion between the shoulder and the bottom end; the bottom-compartment sidewall portion having a larger cross-section than the top-compartment sidewall portion; a plunger having a shaft, a distal end, a proximal end, and a plunger head having a smaller cross-section than the bottom-compartment sidewall portion provided at the distal end; the plunger inserted into the syringe body plunger head first through the bottom-end opening; the plunger head configured and adapted to form a seal when the plunger head engages the top-compartment sidewall, wherein the plunger is axially translatable between a first position where the plunger head is sealingly engaged with the top-compartment sidewall dividing the syringe body into a top compartment and a bottom compartment, and a second position where the plunger head disengages from the top-compartment sidewall establishing a two-way flow communication between the top and bottom compartments; and a bottom closure member having a central aperture in which the plunger shaft is slidably disposed, wherein the bottom closure member is slidable along the plunger shaft between an unsealed position where the bottom-end opening is not sealed and a sealed position sealing the bottom-end opening of the syringe body.

The syringe according to the '194 patent may be used to form a multi-compartment container for storing a variety of medicaments as, for example, medicaments for human use in the form of a dry powder which are mixed with a liquid to form a liquid formulation shortly, before use. Such medicament, for example, may include a variety of drugs, e.g. antibiotics. The shelf life of such mixed dry powder and liquid formulations is limited, and this dictates the need to prepare the formulation only shortly before use. The limited shelf life of the powder and liquid formulation is a result of a loss of activity of an active ingredient in the formula, accelerated oxidation once in solution, etc.

While this syringe has various advantages over conventional syringes, it is a single barreled syringe, requiring either that the compartments be filled in a single location or by the user at the time of use. Additionally, filling the separate compartments of this syringe with different components is cumbersome and limited. Furthermore, it has little flexibility, as in cases where one component may be mixed on one occasion with a second component, while on another occasion, it is preferred to mix the first component with a different component altogether. In addition, if an additional component is required to be added it is not possible to add another compartment to a prepared syringe of defined size and volume.

Another disadvantage of the single body syringe of the '194 patent is the method of filling the syringe. The syringe is assembled and filled, according to one method, by first orienting the body with the two-compartment embodiment of the syringe in an upright position with its top-end opening pointing upwardly. The plunger is then inserted into the syringe body, plunger-head portion first, until the plunger head engages the top-compartment sidewall. This forms a hermetic seal at the bottom of the top compartment near the shoulder portion. The top compartment is then filled with a first component of a medicament, preferably a liquid, through the top-end opening and sealed with a suitable top sealing member or assembly.

Alternatively, the top compartment may be filled by inserting the plunger completely to the end of the top compartment, immersing the open top end in the liquid, then drawing the liquid into the top compartment by pulling the plunger back to its sealed position between the compartments. This method is only practical when the first component of the medicament is a liquid.

Next, the syringe device may be turned 180 degrees, with the sealed top end oriented downwardly, so that the bottom-end opening is facing up. The bottom compartment is filled with a second component of the medicament through the bottom-end opening and sealed with the bung. Filling the bottom compartment while the plunger shaft is disposed through the bottom-end opening is cumbersome and poses various constraints on the filling process. The second component may be a liquid or a powdered solid substance. In this embodiment where a bung seals the bottom opening, the second component may be placed in the bottom compartment in a hydrated form and dried using a lyophilization process.

There is a design concern with the prior art multi-compartment syringes that, prior to use, the compartments be hermetically sealed, so as to prevent, over an extended period of time, accidental pre-mature mixing of liquid or liquid vapor of a component in one compartment with a component in a second compartment. Another design concern with such multi-compartment syringes is that the user should be able to readily inspect the component in any of the compartments just prior to use, in order to verify its useful condition. Yet another concern with many of the multi-compartment syringes is the relatively high cost of manufacture.

Accordingly, it would be very desirable to have a multi-compartment syringe which is formed of two or more separate containers capable of separately storing one or more different components, and which can be joined together as desired, depending upon the components required, and which can farther be extended in situ, if additional components are required. Advantages of such a multi-compartment syringe include the possibility of filling the compartments in different locations and assembling the syringe where and when needed. Additionally, the filling of the separate containers, each having top and bottom sealable openings, is a much easier and more flexible task. Because each component of a multi-component medicament may be stored in separately sealed containers, the components of a medicament may be stored for longer periods without concerns of accidental mixing. The use of such a syringe may also shorten the time required for administering a medicament which is a solution of two components. Each of the assembly units may be provided in various sizes to accommodate different quantities of each component of a medicament, where appropriate. In particular, the dispensing unit may have a pre-selected volume permitting multiple injections of a pre-selected dose of a medicament. In this case, the medicament may be stored in the plunger unit whereas the dispensing unit may have a pre-selected volume permitting multiple injections of a pre-selected dose of a medicament, which is transferred from the plunger unit into the dispensing unit just prior to injecting of the pre-selected dose.

SUMMARY OF THE INVENTION

The syringe assembly of the present invention consists of two basic types of assembly units: a dispensing unit, and a separate, independent plunger unit. The dispensing unit and the plunger unit are assembled together coaxially to form a two-unit syringe assembly for storage or just prior to use. At least the dispensing unit is a container for a material to be dispensed and, by inserting one or more extension units between the dispensing unit and the plunger unit, additional compartments may be added. Each extension unit may contain a different component of a formulation in any predetermined quantity. For purposes of the present application, the terms component, formulation, medicament, mixture, solution, or any combination thereof, can also be referred to as a material.

The syringe assembly of one embodiment of the invention allows the user to store one or more components of a formulation in separate individual units that can be assembled easily into a single multi-compartment syringe assembly, which can store the multiple components separately until they are ready for use, at which time the components may be mixed to form the formulation just prior to dispensing. Each of the assembly units may be a separate container that may be assembled together readily to form a single multi-unit syringe assembly, with each of the assembly units forming a separate compartment.

It is to be appreciated that, because the volumes of the dispensing unit and the plunger unit may be varied in unlimited combinations, this assembly system provides the flexibility of allowing the user to prepare varying quantities of a given formulation, as well as to prepare a complex formulation with multiple components of varying quantities. Each of the assembly units may be provided in various volumes to accommodate different quantities of each component of a formulation where appropriate. In addition, according to one embodiment of the invention, the dispensing unit may be sized to contain a pre-selected volume of a component or mixture to be dispensed, which is stored in the plunger unit and transferred to the dispensing unit before dispensing. Thus, the dispensing unit may be selected to have the appropriate volume for a fixed dosage of a component or mixture.

Alternatively, the plunger unit need not contain a component to be dispensed or mixed, but may be designed to hold only a plunger, and be arranged to dispense a material from a plurality of dispensing units, which are coupled to the plunger unit one at a time.

Another advantage of using the multi-compartment syringe assembly of this invention over the prior art single barrel multi-compartment syringes is that the assembly provides longer storage-life for the components of a formulation and, in most applications, there is no need for special storage conditions of the assembly and/or components, such as refrigeration. Because each component of a multi-component formulation may be stored in separately sealed containers, the components of a formulation may be stored for longer periods without concerns of accidental mixing.

A dispensing unit may be a container for storing a component of a formulation, or for providing a single, pre-measured dose of a component or mixture, the container having an opening at each end of the container body. The bottom end of the dispensing unit may be adapted and configured to engage a plunger unit in order to assemble a multi-compartment syringe assembly. The top end of the dispensing unit may be adapted and configured to engage a dispensing device, such as a hypodermic needle, or a dosage device, etc.

Both ends of the dispensing unit may typically be sealed so that the dispensing unit's content can be protected from any contamination or spillage during storage. And because these seals must be removed in order to assemble the multi-compartment syringe assembly and dispense the contents, the seals are preferably configured to be readily removed or broken, e.g., a breakable or peelable seal. The breakable or peelable seal may comprise a membrane where the membrane may be a foil or a non-metallic membrane, such as a plastic or other polymer membrane, and may have a single-layer or a multi-layered laminate structure. Such membrane seal may be heat sealed along the rims of the dispensing unit's open ends so that it may be peeled off to engage a plunger unit or to attach an appropriate dispensing device. The seal may further comprise a screw-on or pressure-closing cap.

A plunger unit is a second container for storing another component of the formulation or a formulation itself, with an opening at each of the top and bottom ends of the container. The top open end of the plunger unit may be adapted and configured for sealing engagement of the bottom opening of the dispensing unit in order to assemble a two-unit syringe assembly. To form a two-compartment syringe assembly, the upper portion of the plunger unit, which may define a joining sleeve, is inserted into a depending flange defining the bottom portion of the dispensing unit, whereby each assembly unit forms a separate unit of the resulting syringe assembly. The diameter of the inner sidewall of the depending flange is sized for receiving and sealingly engaging the upper portion of the plunger unit.

A plunger having a shaft, a distal end, a proximal end, and a plunger head at the distal end is disposed within the plunger unit for dispensing a material stored in any unit of the syringe assembly, or for selectably providing two-way flow communication between the plunger unit and the dispensing unit. Thus, the head of the plunger sits in the joining sleeve of the plunger unit and preferably forms a fluid-tight seal with the inner sidewall surface of the joining sleeve. According to one embodiment of the invention, the diameter of the head of the plunger is smaller than the diameter of the body of the plunger unit, so as to provide a passage between the plunger head and the inside wall of the body of the plunger unit. At the same time, the plunger head is configured and adapted to form a slidable hermetic seal when it engages the inner sidewall of the dispensing unit.

To lock the units to one another, the outer surface of the joining sleeve may be provided with one or more locking elements, which engage mating locking elements on the inner sidewall of the flange of the dispensing unit. An additional sealing washer or other sealing element may be disposed in the upper portion of the depending flange for engagement by the top edge of the joining sleeve to provide a hermetic seal between the dispensing unit and the plunger unit.

According to a preferred embodiment, the plunger head is movable between a sealed position, where it forms a seal between the plunger unit and the dispensing unit, and an unsealed position, whereby a two-flow communication is formed between the dispensing unit and the plunger unit. The sealed state may be established by positioning the plunger head in the joining sleeve of the plunger unit or in the body of the dispensing unit. In the unsealed state, the plunger head is positioned inside the body of the plunger unit, which has a larger diameter than the plunger head.

A closure member having an aperture is also provided at the bottom of the plunger unit. The plunger shaft is slidably disposed within the aperture of the closure member so that the closure member is slidable along the plunger shaft between a sealed position, hermetically sealing the bottom-end opening of the plunger unit, and an unsealed position where the bottom-end opening is not sealed. When the closure member is in its sealed position, it seals the bottom end of the plunger unit and the plunger can be axially translated between its first position and its second position without moving the closure member. To enable the translation of the plunger without displacing the closure member, the closure member may be configured and adapted so that the friction between the closure member and the sidewall of the syringe body is greater than the friction between the closure member and the plunger shaft. Alternatively, the closure member may have screw threads for screwing onto the body of the plunger unit.

In a three- or more compartment syringe assembly according to the invention, one or more extension units are provided and adapted to be affixed between the dispensing unit and the plunger unit. Each extension unit includes a substantially cylindrical sidewall portion having a sealable opening at each end. According to a preferred embodiment, the diameter of the sidewall portion of the extension unit will be larger than the diameter of the dispensing unit but smaller than the diameter of the plunger unit. The top end of the extension unit may be adapted and configured to engage the bottom end of the dispensing unit, and the bottom end of the extension unit may be adapted and configured to engage the top end of a plunger unit, in order to assemble a multi-compartment syringe assembly. The top and bottom seals are coupled to permit them to slide in tandem inside the syringe assembly.

The syringe assembly may be filled and assembled in a number of ways, according to the particular embodiment. First, the dispensing unit, which constitutes the top compartment, is filled with a desired component, if any. The dispensing unit may be filled through the top-end opening and sealed with a suitable topsealing member, if desired. Alternatively, the top end opening may be sealed first, and the dispensing unit rotated through 180 degrees to permit filling through its larger, bottom end opening. Then this sealable opening is sealed hermetically, permitting the dispensing unit to be stored until needed. The first component may be a liquid, a gel, or a powdered solid substance.

It is a particular feature of the present invention that the component stored in the dispensing unit conveniently may be a powdered solid component. The dispensing unit may be easily filled with a powdered substance through the relatively large bottom-end opening of the dispensing unit. It will be appreciated that it is much easier to inspect a powdered component when it is in the dispensing unit, since the material can be easily viewed through the transparent syringe body, without interference from the plunger shaft, and the state of the component can be determined before use. Thus, the syringe also provides easily viewed tamper evidence. Furthermore, as described below, the assembled syringe assembly of the present invention provides double protection against liquid leakage from one compartment to a second compartment.

Alternatively, the dispensing unit may be a disposable ampoule, for holding a single dose of a medicament for dispensing by the plunger unit.

Next, if desired, the plunger unit is filled. The top-end opening is sealed by a removable seal. The plunger unit is now filled through the bottom-end opening. The plunger head is inserted into the bottom end of the plunger unit, and the closure member is slid along the plunger shaft until it seals the bottom-end opening of the plunger unit. The plunger unit is now rotated through 180 degrees to permit the component to pass around the plunger head towards the bottom portion of the plunger unit. The plunger is now pushed through the plunger unit until the plunger head sealingly engages the inside wall of the joining sleeve. The plunger unit may now be stored until needed.

The second component may be a liquid, gel or a powdered solid substance. To prevent any degradation of a liquid component from prolonged exposure to air during storage, the compartment holding the liquid may be sized to fill completely with the liquid component, minimizing or eliminating any air pockets inside the compartment. Alternatively, any unfilled space in the compartment may be filled with a material, such as nitrogen gas for example, which is inert with the first component.

According to one embodiment of the invention, where a bung seals the bottom opening of the plunger unit, the second component may be placed in the plunger unit in a hydrated form and dried using a lyophilization process. Before the lyophilization process begins, the bung is brought close to the sealable opening so that it almost fits into the sealable opening, and the substantial portion of the bung remains outside the sealable opening. The vacuum created in the plunger unit during the lyophilization process pulls the bung completely into the sealable opening, sealing the bottom-end opening. It will be appreciated that this process can also be performed with a, component in a dispensing unit having a bung as a bottom end seal.

At the time of assembling the syringe assembly, the dispensing unit is coupled to the plunger unit, as by means of mating locking elements in the plunger head and the bottom end seal of the dispensing unit. Thus, the bottom end seal of the dispensing unit forms an integral part of the plunger head. Once assembled, this syringe assembly operates like a single barrel, multi-compartment syringe.

The present invention also provides processes for preparing multi-unit syringe assemblies. The process includes:

(a) providing a dispensing unit having a dispensing unit body and a sealable opening at each of its top and bottom ends;

(b) providing a separate, independent plunger unit having a plunger unit body and a sealable opening at each of its top and bottom ends;

(c) placing a plunger within the plunger unit, the plunger having a plunger head adapted to form a seal closing the top opening of the plunger unit, and (d) coupling the dispensing unit coaxially to the plunger unit to form a two-unit syringe assembly.

The process may further include providing at least one independent extension unit having a cylindrical body and sealable openings at it top and bottom end, and coupling the extension unit between the dispensing unit and the plunger unit to form a three- or more unit syringe assembly.

The process may further include the steps of filling the dispensing unit and/or the plunger unit before coupling the units to form the syringe assembly. Alternatively, the process may further include the steps of filling the dispensing unit and/or the plunger unit after coupling the units to form the syringe assembly.

The present invention also provides processes for preparing multi-unit syringe assemblies for holding and storing one or more components of a formulation separately until the units are assembled into a single multi-unit syringe for dispensing the formulation or for mixing the contents of the compartments prior to dispensing. The process includes:

(a) providing a dispensing unit having a housing and an opening at each of its top and bottom ends;

(b) sealing one end of the dispensing unit;

(c) introducing a first component of a formulation, if there is more than one, into the dispensing unit through the other end and sealing that end;

(d) providing a separate, independent plunger unit having a plunger unit body and an opening at each of their top and bottom ends;

(e) placing a plunger within the plunger unit, the plunger having a plunger head adapted to form a seal closing the top opening of the plunger unit, the plunger head movable between a sealed position and an unsealed position; the plunger being placed in the plunger unit in the sealed position;

(f) introducing a different component of the formulation, or a medicament if there is only one, into the plunger unit through the sealable filling opening of the plunger unit; and (g) sealing the sealable filling opening.

Once the dispensing units and the plunger units are prepared and sealed, they can be stored for extended periods of time until they are ready to be assembled into a single multi-compartment syringe to dispense the contents of the plunger unit or the dispensing unit, or to mix the contents of both units into a formulation for dispensing.

After the user has assembled the filled assembly units into a multi-compartment syringe and mixed and dispensed the contents of the syringe, the assembly units, particularly the plunger unit, can be reused. The assembly units may be disassembled and then refilled, or different dispensing units may be affixed, one at a time, to the plunger unit, for dispensing the contents of the dispensing units.

Furthermore, the assembly units, according to one embodiment of the present invention, may be filled and pre-assembled into a multi-compartment syringe and then stored as an assembly until the contents of each unit are ready to be mixed and dispensed. It is to be appreciated that in the assembled state, each dispensing unit and plunger unit forms a separate compartment of the multi-compartment syringe, preventing the contents of the units from mixing prematurely.

The syringe assembly of the present invention is also useful for providing multiple injections of a pre-selected dosage of a single medicament. In this case, the plunger unit may be filled with the desired medicament and sealed with the plunger head. The dispensing unit may consist of an empty container of a pre-selected volume for holding the pre-selected dosage, which is filled from the plunger unit when the plunger head is moved to the unsealed position, permitting flow communication between the plunger unit and the dispensing unit. When the dispensing unit is full, the plunger head is moved to the sealed position, and the pre-selected dosage is ready for dispensing.

The syringe assembly of one embodiment of the present invention permits multiple use of the plunger unit with an unlimited number of dispensing units, one at a time. According to this embodiment, the plunger unit does not contain a component of the medicament, and merely serves to press a bottom end seal of the dispensing unit so as to dispense the contents of the dispensing unit. Additionally, a single plunger unit can be used repeatedly with a combination of extension units with dispensing units, for dispensing, or for mixing and then dispensing, the components in the combined extension and dispensing units. The invention will now be illustrated in some specific embodiments directed to two and three-compartment syringe assemblies, fitted with a hypodermic needle as the dispensing device. It will be appreciated by one of ordinary skill in the art that the same principle is also applicable to form containers with additional separate components, and containers for other applications and areas where it is desired to store components of multiple-component formulations separately in individual containers and then assemble the individual assembly units into a single multi-compartment syringe which will store the components separately in such multi-compartment containers which may later be mixed to form and dispense the formulation.

The drawings are only schematic and are not necessarily to scale.

DETAILED DESCRIPTION OF THE INVENTION

Some examples of the syringe assemblies of the present invention are provided to illustrate various specific configurations and examples of the invention. The invention should not be regarded as being limited to these embodiments. The syringe assemblies may also be used for different uses, e.g., a syringe assembly of two or more units used as compartments for medicinal formulations, dietary powders to be reconstituted with a liquid or other mixtures wherein one compartment contains one component and the other compartment contains another component to be mixed to form a formulation. Alternatively, a syringe assembly according to the present invention is formed of a plunger unit and a dispensing unit, wherein the plunger unit holds a medicament and the dispensing unit is adapted to hold a pre-selected dose of the medicament for administering it. According to a preferred embodiment, using a dispensing unit of a small volume relative to the volume of the plunger unit, allows the user to repeat the administering of the pre-selected dose until the entire medicament has been dispensed. Alternatively, a syringe assembly may be formed of a plunger unit adapted to be coupled to a plurality of dispensing units, one after the other, for dispensing a medicament from the dispensing units by the plunger unit.

Figure 1:
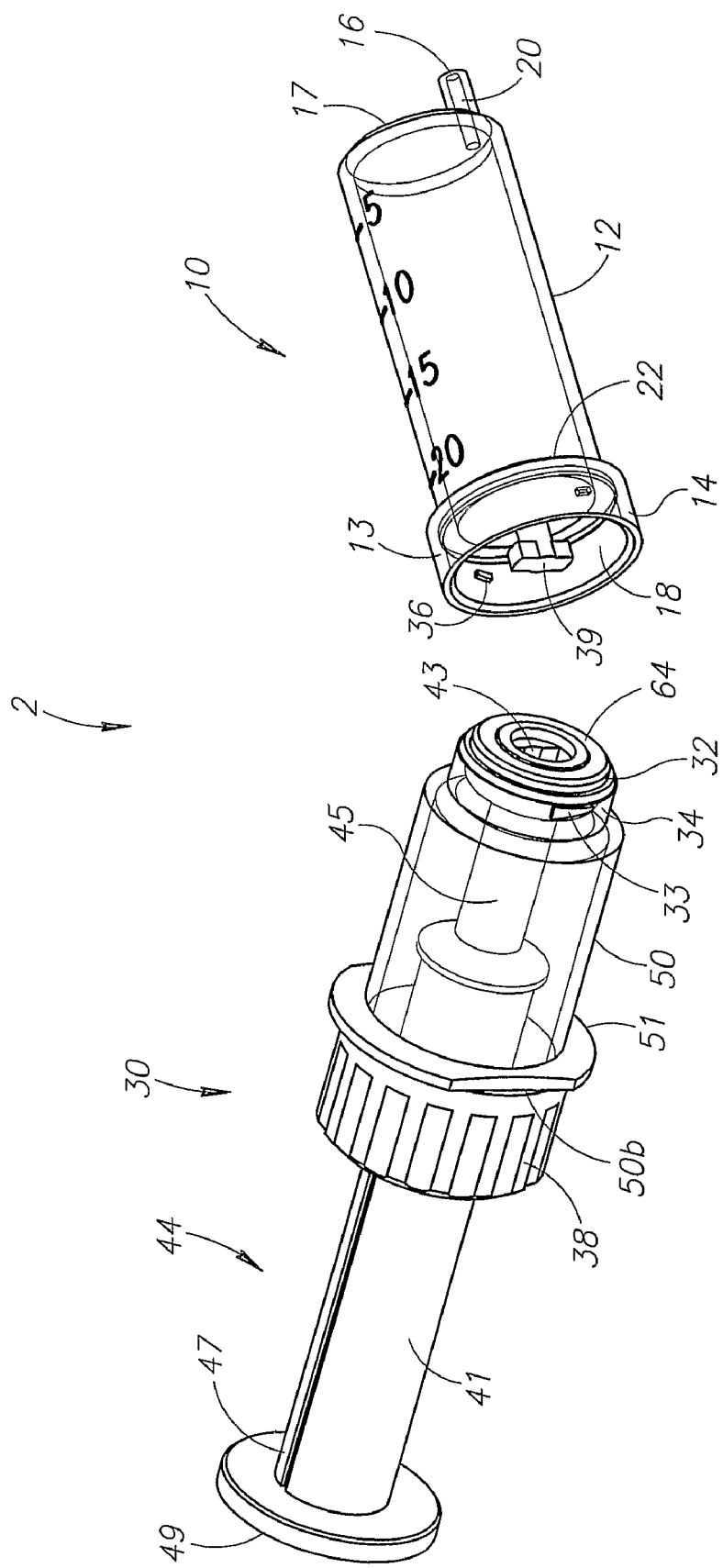
FIG. 1 is a perspective view of an embodiment of the syringe assembly of the invention in a non-assembled state, having two compartments where the syringe bodies are illustrated as being translucent in order to show the internal structures of the syringe.
Figure 2:
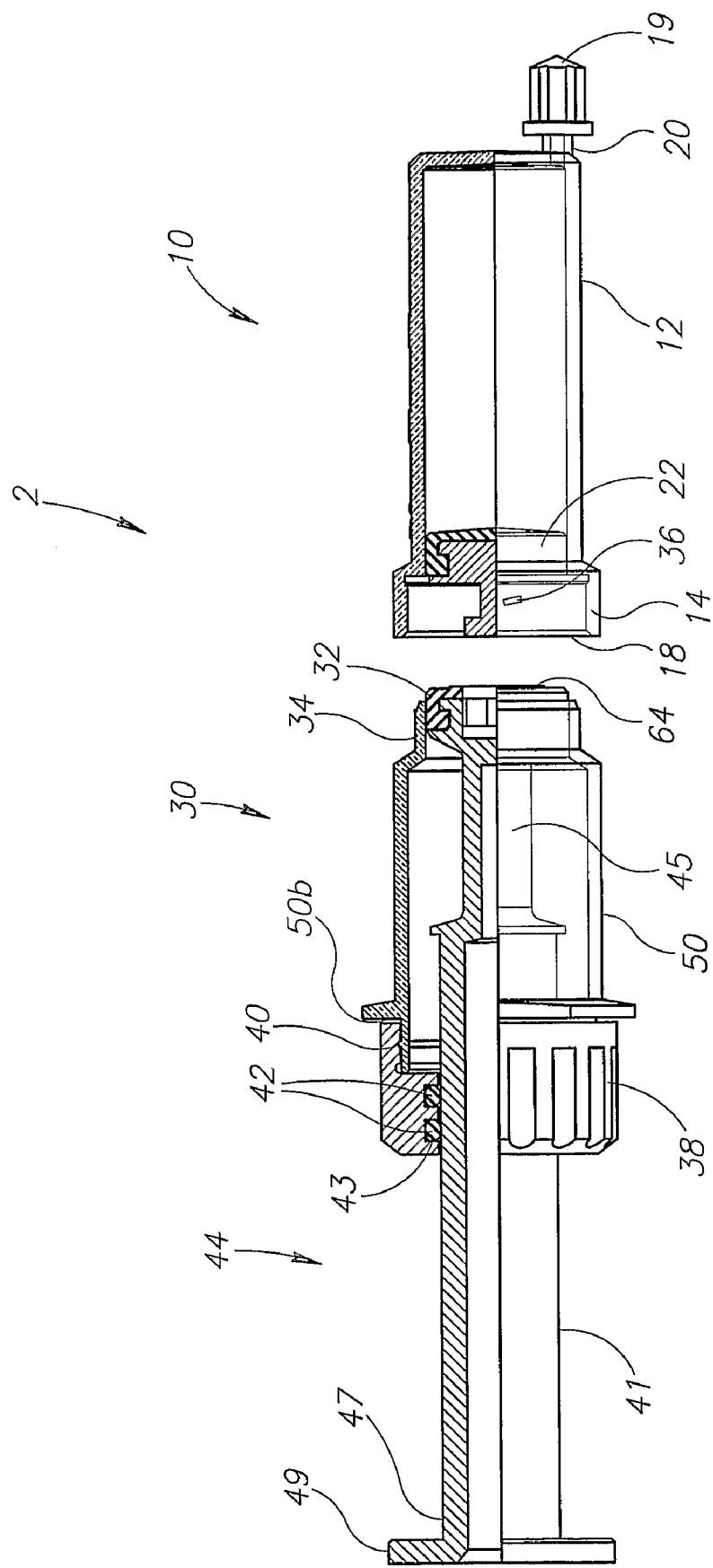
FIG. 2 is a partial sectional view of the syringe assembly of FIG. 1.

FIGS. 1 and 2 illustrate a syringe assembly 2 in a non-assembled state, including a dispensing unit 10 with a body 12, a top opening 16 and a bottom opening 18. Preferably, body 12 is substantially cylindrical. The bottom portion of body 12 may define a depending flange 14 adapted and configured for a sealed locking engagement with a plunger unit 30.

The top portion of body 12 may define an open ended nipple 20 with top-end opening 16. Nipple 20 may be adapted and configured for attaching an appropriate dispensing device, e.g. a hypodermic needle (not shown). For illustrative purposes, in this embodiment dispensing unit 10 is provided with a screw thread for sealing attachment of a removable screw cap 19 (shown in FIG. 2) or a dispensing device. It will be appreciated that the top portion 17 of body 12 may be sealed, for example, by a removable cover member (not shown). According to one embodiment, the cover member is provided with a screw thread on a first end for sealing attachment to body 12 having matching screw threads (not shown), and a screw thread on a second end for sealing attachment of a desired dispensing device having matching screw threads (not shown). Alternatively, the cover member may be replaceable by a dispensing device.

Dispensing unit 10 may be empty or may be filled with a medicament or a component of a formulation, which may typically be a liquid, a powdered substance, or a gel, etc. During the storage of the dispensing unit 10, the top and bottom openings 16 and 18 respectively, may be sealed to prevent contamination or spoilage of the contents of the dispensing unit or spillage thereof. Opening 16 may be sealed with a membrane (not shown) with or without cap 19. Opening 18 may also be sealed with a membrane (not shown) or with other suitable sealing methods (e.g., screw caps, or a bung 22). The seals are preferably readily removable so that a plunger unit 30 and a dispensing unit 10 may be assembled into a multi-compartment syringe for dispensing, and possibly mixing, of a formulation. The sealing membranes may be foils or non-metallic membranes, and may have a single or a multi-layered structure. The membranes are preferably heat sealed to the open ends of the dispensing unit in such manner that they may be peeled off.

Syringe assembly 2 further includes a plunger unit 30 which is engaged with dispensing unit 10 to form a two-compartment syringe assembly. Plunger unit 30 has a body 50. Preferably, body 50 is substantially cylindrical. The top portion of body 50 defines a neck portion having an inner sidewall diameter smaller than the inner sidewall diameter of body 50 and an outer sidewall diameter smaller than the inner sidewall diameter of flange 14, and forming a joining sleeve 34, having a top opening 32. When plunger unit 30 and dispensing unit 10 are assembled, joining sleeve 34 is inserted into flange 14 of dispensing unit 10. The outer sidewall of joining sleeve 34 maybe provided with two or more slightly slanted, peripherally extending ribs 33 configured for locking engagement with at least two matching ribs 36 peripherally extending from the inner sidewall of the flange 14 of the dispensing unit 10. This provides a friction-fitting joint between the inner sidewall of flange 14 and the outer sidewall of joining sleeve 34. A sealing washer 13 or other sealing element is provided in the upper portion of flange 14 for engagement by the top edge of the joining sleeve 34, to provide a hermetic seal between the dispensing unit and the plunger unit in the assembled syringe. The internal diameter of sealing washer 13 is substantially equal to the inner sidewall diameter of body 12.

Plunger unit 30 also includes a plunger 44. The plunger 44 may be axially displaced between a sealed position and an unsealed position. The plunger 44 consists of a user manipulable plunger shaft 41, having a distal end 45 and a proximal end 47 and is provided with a substantially cylindrical plunger head 64 at distal end 45. The outer diameter of the plunger head 64 is substantially the same as the inner sidewall diameter of joining sleeve 34, and substantially the same as the inner sidewall diameter of dispensing unit body 12. Thus, in the sealed position, plunger head 64 sealingly engages the inner sidewall surface of joining sleeve 34 thereby closing opening 32 in a fluid-tight manner, and forming a hermetically sealed partition between dispensing unit 10 and plunger unit 30. In an unsealed position, plunger head 64 is axially retracted inside the compartment defined by plunger unit body 50, where the inner sidewall diameter is larger than the outer diameter of plunger head 64, which allows the component in this compartment to flow around plunger head 64. Plunger head 64 is preferably made of an elastomer having characteristics (e.g. hardness, elasticity, etc.) that is suitable to provide the desired sealing quality. The particular elastomer selected for the plunger head 64 should also be chemically inert with respect to the particular medicament or components with which plunger head 64 may come in contact. A thumb rest 49 may be provided on proximal end 47 of plunger 44 with which a user may urge the plunger 44 into the syringe assembly 2 to dispense of its contents. In the unsealed position, plunger head 64 is disengaged from sealable opening 32, allowing a two-way flow-communication between the compartment defined by body 50 and the compartment defined by body 12, through opening 32. The diameter of the inner sidewall of body 12 is sized for receiving and sealably engaging plunger head 64.

According to one embodiment, illustrated in FIG. 1, dispensing unit seal 22 is a bung having substantially the same outer diameter as body 12 of dispensing unit 10. Bung 22 is adapted and configured to lockingly engage plunger head 64. Preferably, the locking mechanism is a bayonet lock. As illustrated, the bayonet locking mechanism includes an elongated locking member 39 fitted to pass through a matching recess 43 in plunger head 64 and lock one to the other by turning the assembly units, or either one of them, relative to one another, simultaneously with locking flange 14 to joining sleeve 34. It will be appreciated that the locking mechanism is preferably releasable.

The syringe assembly 2 also includes a threaded closure element 38 for sealing the bottom-end opening 50b of the plunger unit 30. The closure element 38 is sized to receive the bottom end of the body 50 of plunger unit 30, and is provided with screw threads 40 along its inner sidewall, shown in FIG. 2. Body 50 is provided with mating screw threads (not shown) near its bottom end so that the closure member 38 can be screwed onto body 50 and seal the bottom opening of the plunger unit 30. Closure member 38 mechanically prevents accidental or unwanted removal of plunger 44 out of plunger unit 30.

Closure element 38 has a central aperture along its longitudinal axis so that plunger 44 is received through the central aperture of closure element 38 which can be moved up and down the plunger shaft 41 until it abuts against a protruding flange 51 near the bottom-end opening 50b of body 50. Closure element 38 preferably includes a sealing washer (not shown) for sealingly engaging the bottom-end opening 50b of the plunger unit. Part of the inner surface of closure element 38 adjacent the central aperture may be provided with a plurality of inner sealing ribs (not shown), or a plurality of grooves 43 for receiving o-rings 42, or other annular seals, for sealingly engaging the plunger shaft 41. These annular seals may be configured to form hermetic seals with the mating surface through compression. The bottom closure element 38 may be made of a single material or formed as a composite, but preferably at least the sealing ribs or the o-rings which sealingly engage plunger shaft 41, and the inside surface of closure element 38 which sealingly engage the body 50, are made from an elastomer.

When the closure element 38 is positioned in its sealed position, preferably plunger 44 can be withdrawn partially from plunger unit 30 without dislodging closure element 38 from its sealed position in the bottom-end opening 50b of body 50 of the plunger unit. This allows the plunger head 64 to be disengaged from the sealable opening 32 of joining sleeve 34 to establish communication between the plunger unit and the dispensing unit without unsealing the bottom-end opening of the plunger unit.

According to another embodiment of the present invention, closure element may be a bung (not shown). To enable the translation of plunger 44 without dislodging the closure element 38 where it is a bung, from its sealed position, closure element 38 may be configured and adapted so that the friction between the outer surface of closure element 38 and the inner sidewall of body 50 is greater than the friction between closure element 38 and the plunger shaft 41. In this embodiment, the frictional forces between closure element 38 and the plunger unit body 50 and plunger shaft 41 may be controlled by varying the number of the sealing elements at each sealing surface. Alternatively, it will be obvious to one of ordinary skill in the art that the same result could be achieved by many other methods. For example, the dimensions of the sealing elements, such as their widths and thicknesses, may be varied to achieve the desired frictional forces at each sealing interface without necessarily varying the number of the sealing elements.

According to one embodiment of the invention, illustrated in FIGS. 1 and 2, bottom opening 18 of dispensing unit 10 is sealed by a bung 22, adapted and constructed to frictionally seat in body 12 and provide a bottom-end seal of the dispensing unit compartment. Similarly, the top-end opening 32 of plunger unit 30 is sealed by plunger head 64, adapted and constructed to frictionally seat in joining sleeve 34 and seal the plunger compartment.

Figure 3:
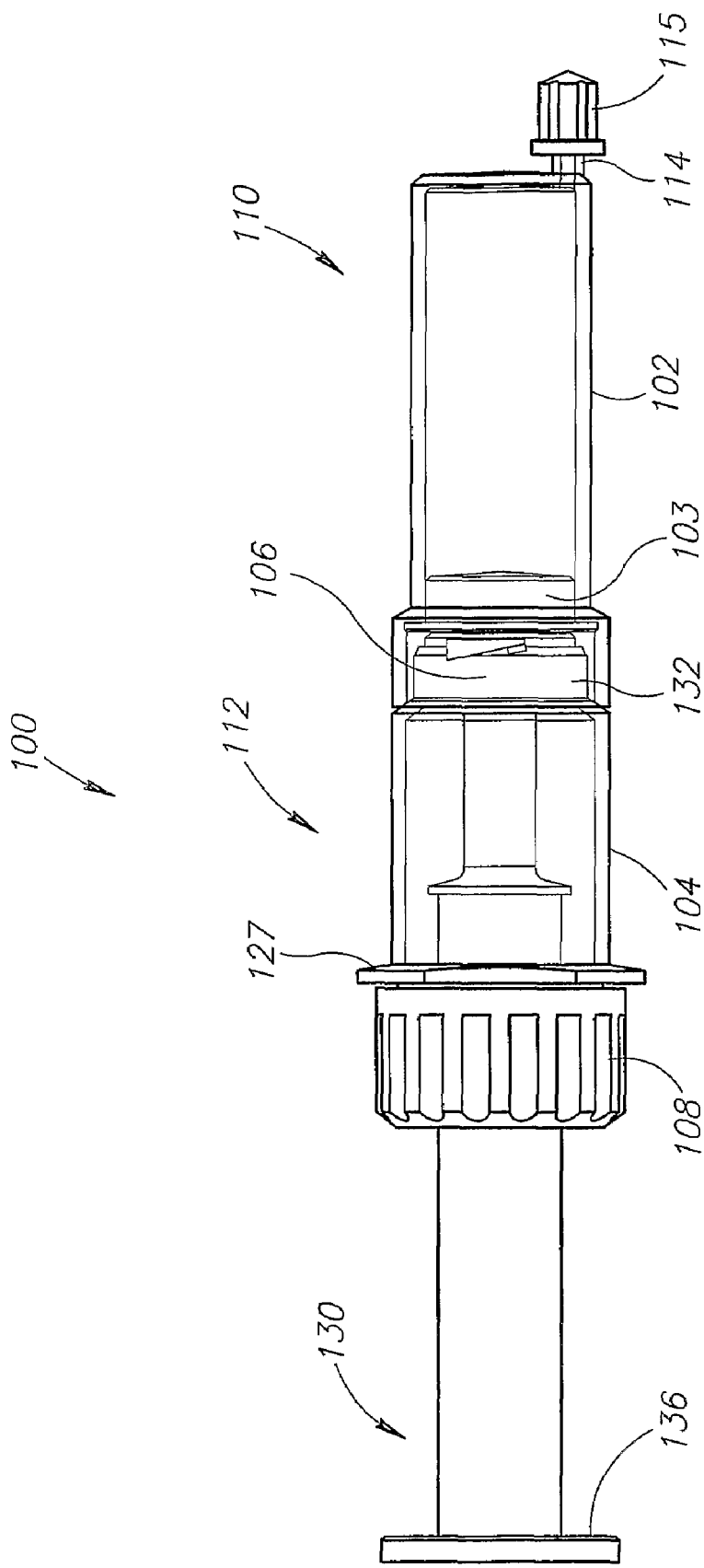
FIG. 3 is a perspective view of the syringe assembly of FIG. 1, when the two compartments have been assembled to form a single syringe.
Figure 4:
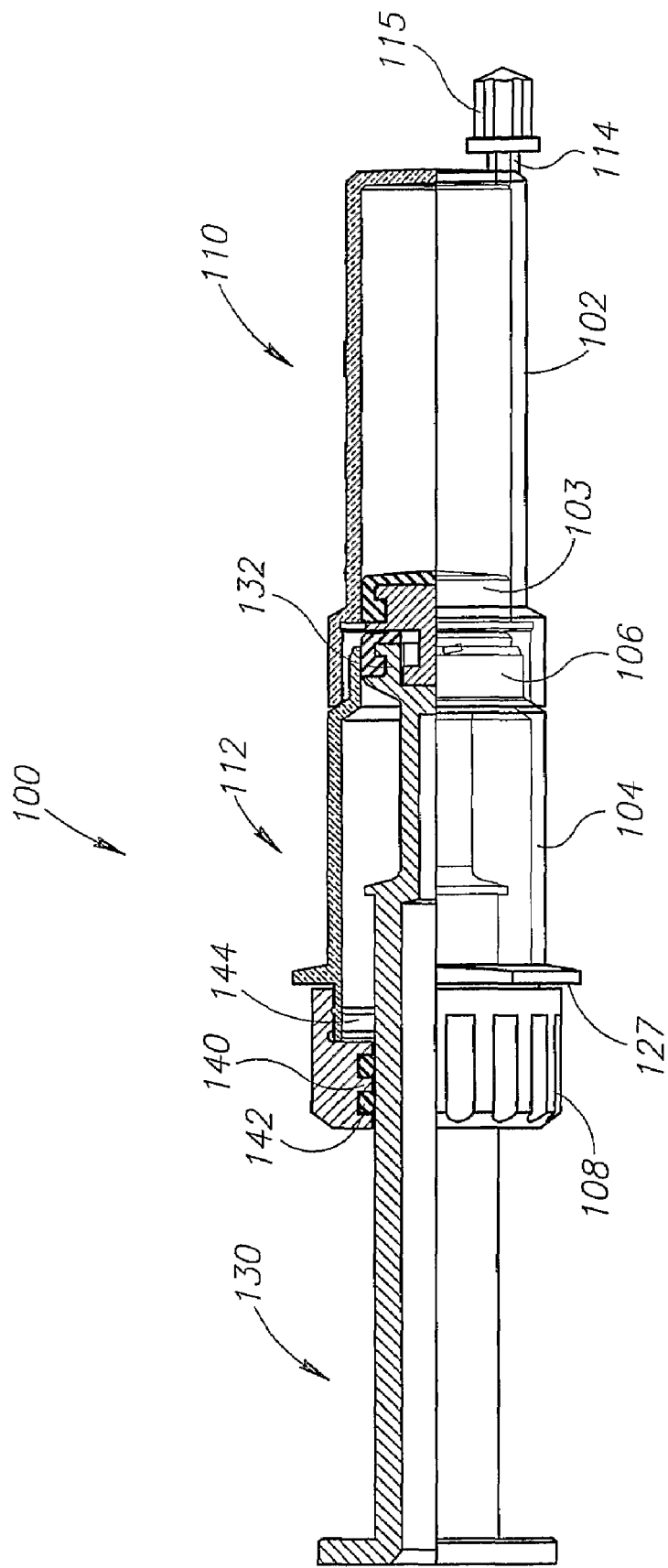
FIG. 4 is a partial sectional view of the syringe assembly of FIG. 3, where the sealing elements of the two compartments have been joined to one another.

FIGS. 3 and 4 illustrate a fully assembled syringe assembly 100, which is substantially similar to the syringe assembly 2 of FIG. 1, with plunger unit 112 and dispensing unit 110 in their sealed configuration, each holding a component of a formulation. Plunger head 132 lockingly engages a bung 103 sealing bottom-end opening 116 (see FIG. 5) of dispensing unit 110. Plunger 130 is positioned inside plunger unit 112 so that the whole plunger head 132 sealingly engages joining sleeve 125 (see FIG. 5), thereby sealing the sealable opening 124 (see FIG. 5) of plunger unit 112. Thus, dispensing unit 110 and plunger unit 112 form a single syringe assembly, temporarily partitioned by plunger head 132 and bung 103 lockingly engaged to one another. The seal formed by the plunger head 132 and bung 103 against the inner sidewalls of bodies 104 and 102, respectively, may be hermetic so that two components of a medicament or other formulation may be stored separately in each compartment until ready to be mixed. Disengaging plunger head 132 from joining sleeve 125 by retracting plunger 130 would allow a two-way flow-communication between the compartment defined by plunger unit 112 and the compartment defined by dispensing unit 110.

In this fully assembled and ready-for-storage configuration, closure element 108 sealingly engages the bottom-end of body 104 of the plunger unit 112, plunger head 132 hermetically sealing the top-end opening 124 (see FIG. 5) of the plunger unit 112, and bung 103 hermetically sealing the bottom-end opening 116 of dispensing unit 110.

The top-end opening of nipple 114 of the dispensing unit is removably sealed with a top sealing member 115 or an assembly which is configured to be removable when desired; for example, when the contents of the syringe assembly 100 have been mixed and are ready to be dispensed. Top sealing member 115 may be a cap as shown in FIG. 3. In this embodiment, top sealing member 115 is a screw cap. Cap 115 is provided with screw threads (not shown) and nipple 114 of dispensing unit 102 is also provided with screw threads so that cap 115 can be screwed onto dispensing unit 102 to seal the top end opening of nipple 114.

It will be apparent to those skilled in the art that top sealing member 115 and nipple 114 may be configured to sealingly engage each other in a variety of ways that may be appropriate and suitable for a particular application. For example, the top sealing member 115 may be a foil or a membrane (not shown) made of a suitable material that may be heat sealed along the top rim of nipple 114. The heat sealed membrane may be peeled away to unseal the top-end opening of nipple 114 when the syringe assembly 100 is ready to be used.

In a typical intended use, a dispensing unit 110 would be sealingly engaged to the top end of a plunger unit 112 whereby the dispensing unit and the plunger unit form the upper and lower compartments of a two-compartment syringe assembly respectively. The two-compartment syringe may be assembled without breaking the seal formed by plunger head 106 and bung 103, and may be used to store the components in assembled fashion and later controllably remove the seal by retracting plunger shaft 130 and unsealing top-end opening 124 of plunger unit 112, and bottom-end opening 116 of dispensing unit 110, to mix the components and form the formulation. Since the outer surface of plunger head 106 has a smaller diameter than plunger unit body 104, axially moving the locked plunger head 106 and bung 103 inside body 104 provides two-way flow communication around the plunger head, thereby allowing the components of the two-compartment syringe assembly to mix.

Figure 5:
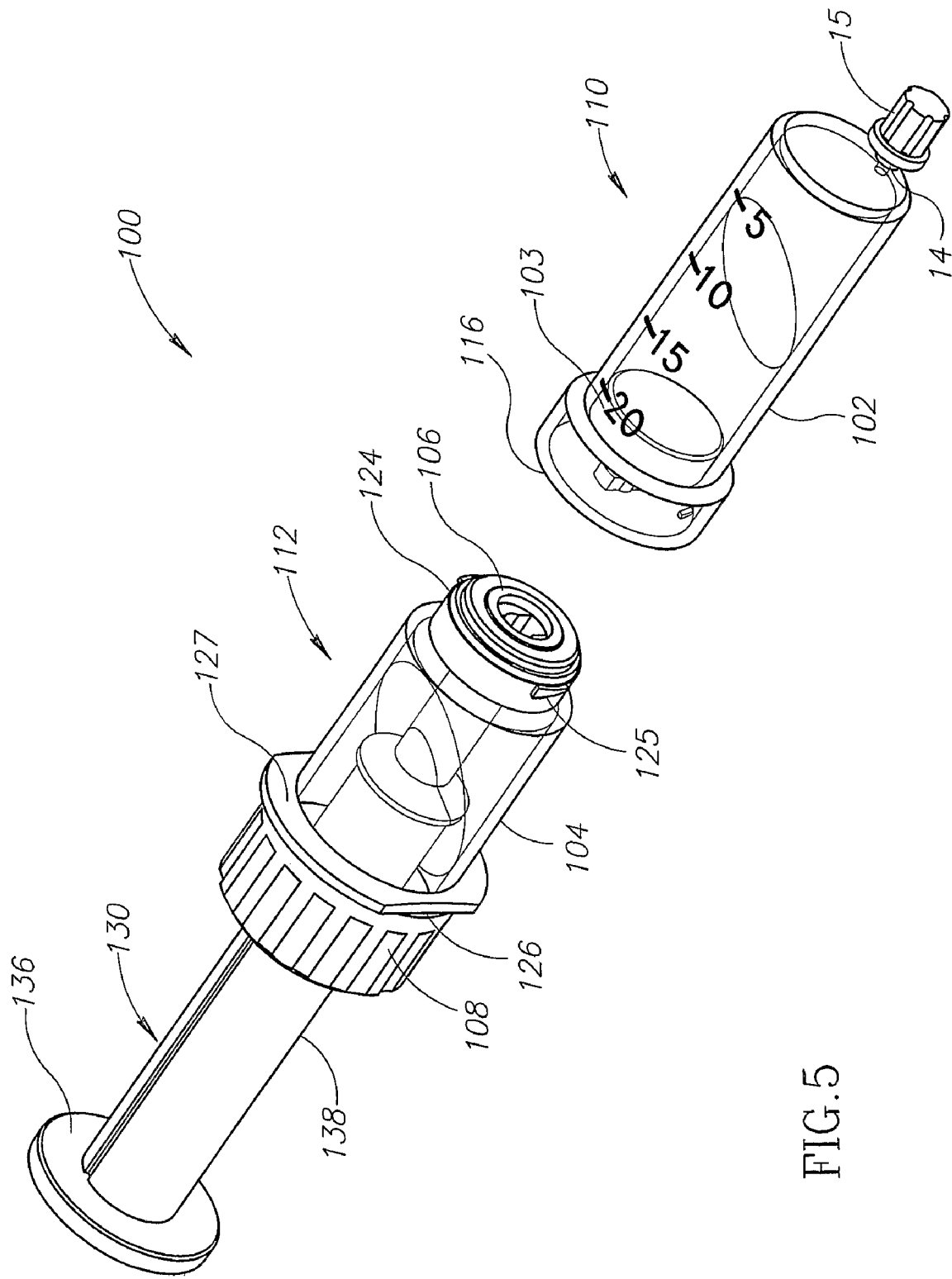
FIG. 5 is a perspective view of the syringe assembly of FIG. 1, illustrating the syringe assembly in an interim stage in the process of filling and assembling the syringe assembly, where the dispensing and plunger units have been filled with desired substances and sealed.

FIG. 5 is a perspective illustration of the syringe assembly 100 in an interim stage in the process of filling and assembling the syringe assembly, where the dispensing and plunger units have been filled independently with desired substances and sealed. The dispensing unit 110 has been filled with the first component of a medicament. The top-end opening of a nipple 114 has been sealed with a cap 115 and the opposite end by a bung 103. The plunger unit 112 has been filled with the second component of a medicament. The bottom-end opening 126 has been sealed with a closure element 108 and the opposite end by a plunger head 106.

Figure 6:
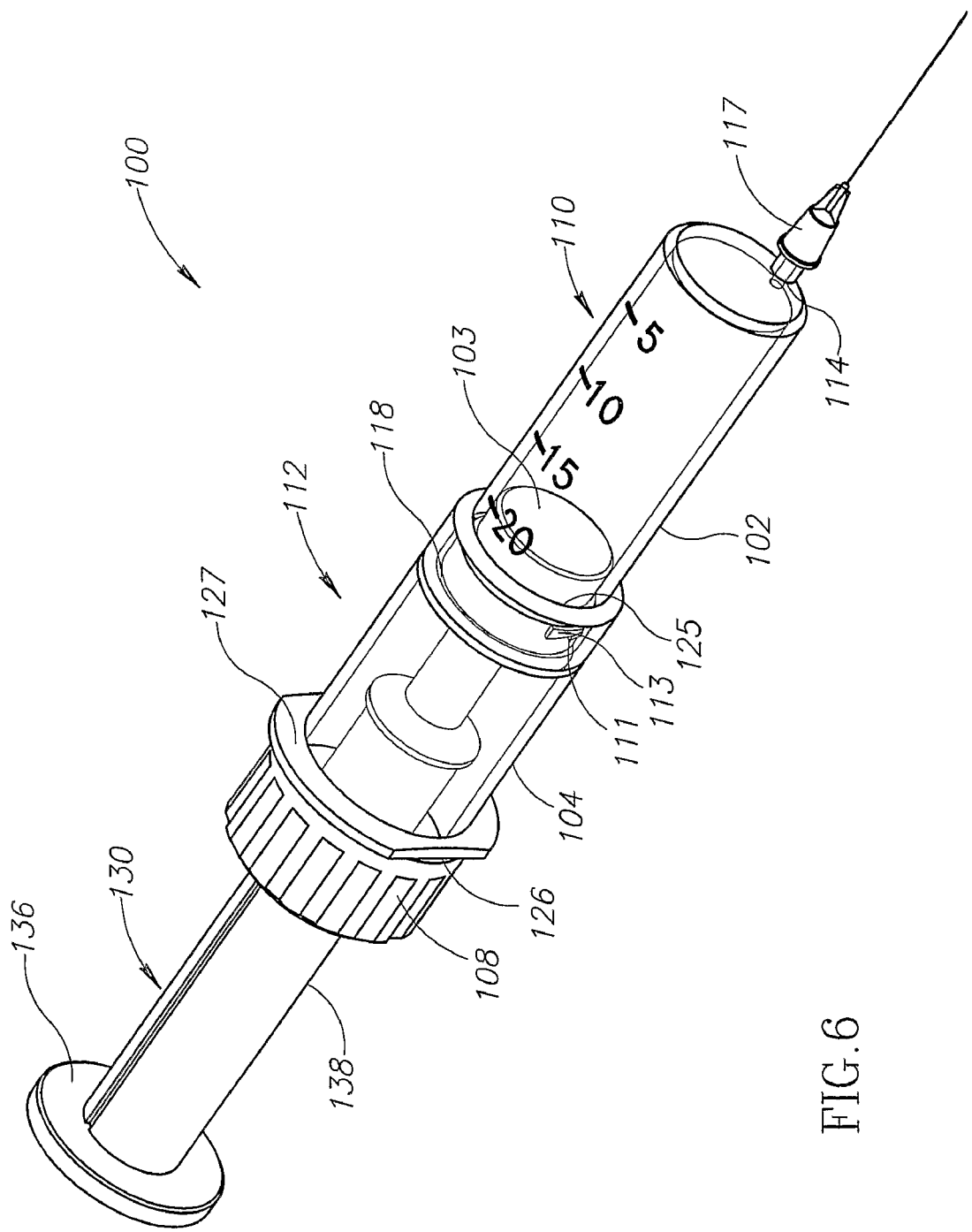
FIG. 6 is a perspective view of the syringe assembly of FIG. 5, showing the fully assembled syringe, where the cap has been removed from the top-end opening and replaced with a hypodermic needle for dispensing the medicament.

The process of filling and assembling the syringe assembly 100 will now is described with the aid of FIGS. 5 and 6. A plunger 130 is positioned inside the plunger unit body 104 in the sealed position, and plunger head 106 seals top-end opening 124 of plunger unit 112. The compartment defined by the plunger unit body 104 may be filled with a component of a formulation through sealable filling opening 126 on the bottom side of the plunger unit 112. Sealable filling opening 126 may then is sealed with closure member 108.

Alternatively, the compartment defined by the plunger unit body 104 may be more conveniently filled by sealing top end opening 124 with a foil or a non-metallic membrane having a single or multi-layered structure. The plunger unit may now be rotated through 180 degrees and filled through sealable bottom end opening 126. Closure member 108 is mounted about shaft 138 of plunger 130. Plunger 130 may now be positioned inside the plunger unit body 104 and the plunger unit sealed by closure member 108.

Yet another option is to position plunger 130 inside the plunger unit body 104 where plunger head 106 is in the unsealed position, and sealably close closure member 108. The plunger unit is now filled through the top end opening 124 and the plunger head 106 is moved to a sealing position inside joining sleeve 125 of plunger unit 112. This is possible due to the fact that the outer diameter of the plunger head is smaller than the inner sidewall diameter of plunger unit body 104.

The dispensing unit may be filled as follows. The bottom-end opening 116 of a dispensing unit 110 is sealed by a bung 103. The dispensing unit 110 can be filled with a desired component of a medicament through the top-end opening of nipple 114. Once the dispensing unit 110 is filled, it may be sealed by closing the nipple 114, as with a screw cap 115.

According to another embodiment, the top opening of the dispensing unit body 102 is sealed by a threaded cover member (not shown) provided with a screw thread on a first end for sealing attachment to body 102, and a screw thread on a second end for sealing attachment of a desired dispensing device. In this embodiment, the bottom-end opening 116 of a dispensing unit 110 is sealed by a bung 103, and the threaded cover member removed. The dispensing unit may now easily be filled through the top opening, and the closed by the threaded cover member.

Alternatively, the top-end opening of nipple 114 of dispensing unit 110 is sealed, as with cap 115. The dispensing unit 110 is now oriented in an upside down position with its bottom-end opening 116 pointing upwardly. The dispensing unit 110 can now be easily filled with a desired component of a medicament through the relatively large bottom-end opening 116. This embodiment is particularly suitable for storing a powdered component in the dispensing unit, since its translucent or transparent sidewall permits easy viewing of the component before use, to permit the user to inspect the physical condition of the component in the dispensing unit prior to use. Once the dispensing unit 110 is filled, it may be sealed by inserting a bung 103 into bottom-end opening 116. The dispensing unit may now be stored until required for assembly prior to use.

According to another filling option, the syringe assembly is first assembled, by coupling the dispensing unit to the plunger unit. In this case, a plunger 130 having a plunger head 106 sized to fit the inner sidewall of body 102 is pushed into body 102 of dispensing unit 110. Top-end opening 114 is opened or fitted with a hypodermic needle 117. The dispensing unit 110 may then be filled from a conventional medicament bottle by immersing the open top end in the first component liquid, then drawing the liquid into the dispensing unit by retracting plunger 130 back to withdraw a desired quantity. The dispensing unit 110 may be dimensioned so that when the plunger is withdrawn back to the filled position, the dispensing unit 110 will be filled with a predetermined desired amount of the first component. In this case, plunger unit 112 may be filled before assembly of the syringe assembly. Alternatively, after filling the dispensing unit, closure element 108 is opened and moved along the shaft of the plunger so that the plunger unit may be filled through the bottom end opening. Once it is filled, plunger unit 112 may be sealed by closure element 108.

To prevent any degradation of a liquid component from prolonged exposure to air during storage, the plunger unit or the dispensing unit may be filled completely with the liquid component, minimizing or eliminating any air pockets inside the unit when sealed. Alternatively, the filling process may be conducted under a vacuum or an inert gas environment so that even if the unit is not completely filled with the liquid component, there would not be any air trapped inside the unit after being sealed.

It will be appreciated that the dispensing and plunger units of the invention may be filled with different components and in different locations, and can be sealed and stored separately prior to assembly and use.

FIG. 6 illustrates the fully assembled syringe assembly 100 ready for use. The syringe assembly 100 now consists of two completely sealed compartments—the dispensing unit 110 and the plunger unit 112—where each compartment is holding a component of a medicament, coupled together until ready to be mixed just prior to use. Coupling of the two units, according to the illustrated embodiment, is as follows. Sealing washer 13 (see FIG. 1) is disposed in depending flange 118. Joining sleeve 125 of the plunger unit 112 is inserted into depending flange 118 of the dispensing unit 110. At the same time, the bayonet locking mechanism 39 (See FIG. 1) on bung 103 engages matching recess 43 (See FIG. 1) in plunger head 106. The dispensing unit is now rotated relative to the plunger unit, in order to seal the separate units to form a single syringe assembly. As can be seen in FIG. 6, the peripherally extending ribs 113 on joining sleeve 125 of body 104 of the plunger unit 112 have been rotated to engage two matching ribs 111 peripherally extending from the inner sidewall of the flange 118 of the dispensing unit 110, and the plunger head 106 lockingly engages the bung 103.

In the embodiment where the bottom end opening of the dispensing unit is sealed by a membrane or laminate, assembly of the syringe assembly is accomplished by removing the seal from the bottom end of the dispensing unit, when in an upside down position, and locking the two units together, as described above. Plunger head 106 positioned inside joining sleeve 125 provides a sealed partition between the two compartments of the syringe assembly, preventing flow communication between the two units until ready for dispensing.

Then, as shown in FIG. 6, cap 115 may be removed and a syringe needle 117 may be attached to the top-end opening of nipple 114. Depending on the application, other dispensing apparatus may be attached to the top-end opening to dispense the medicament or any other formulation.

Figure 7:
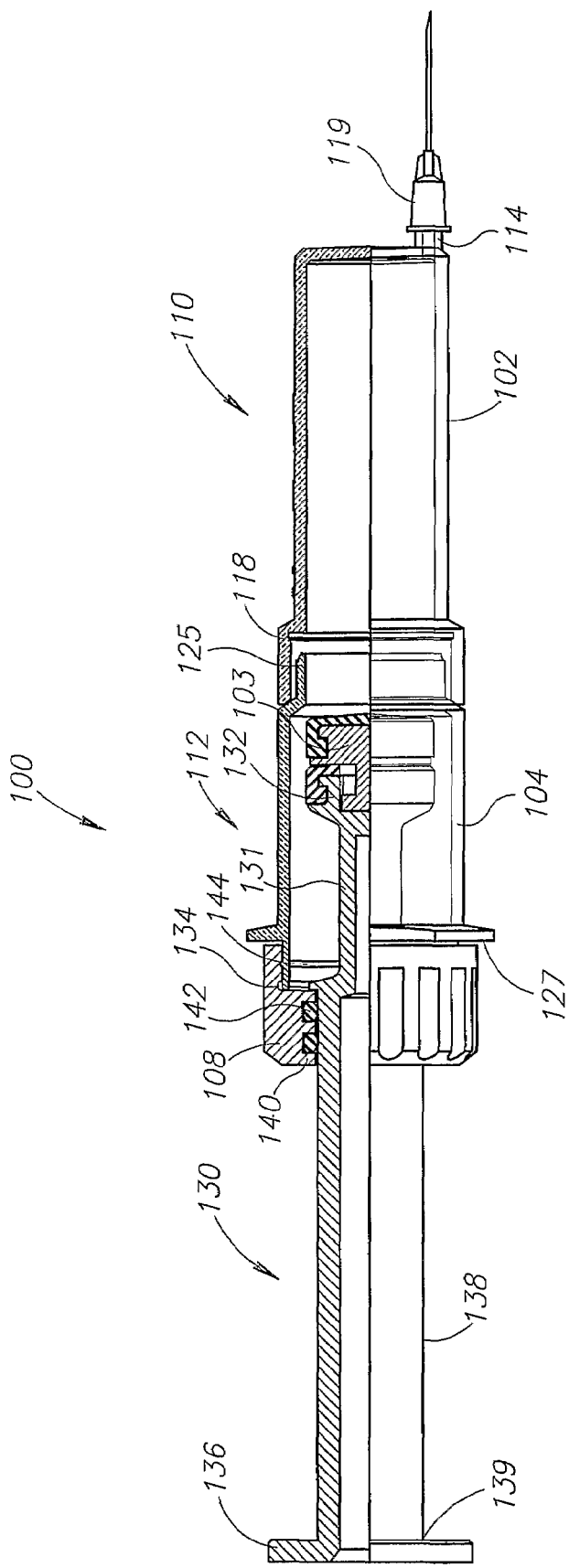
FIG. 7 is a partial sectional view of the syringe assembly of FIG. 6, where the plunger has been retracted into the plunger unit so that the two compartments are in communication with one another allowing the contents of the two compartments to mix.

The process involved in preparing and dispensing the medicament from the two components stored in the syringe assembly 100 will now be described with reference to FIGS. 7-9. In order to mix the two components of a medicament stored in the syringe assembly 100, the plunger 130 is first retracted so that the plunger head 132 disengages from the joining sleeve 125, as illustrated in FIG. 7. It will be appreciated that withdrawing the plunger 130 moves the plunger head 132 and bung 103 lockingly engaged to the plunger head, into the plunger unit whose body 104 has a larger inner sidewall diameter than the inner sidewall diameter of the joining sleeve in which it was sealingly seated, thereby permitting two-way flow communication between the plunger unit and the dispensing unit. As known, the retraction of plunger 130 may be limited by a vacuum force that it may create inside syringe assembly 100. However, since achieving the flow communication between the two units of the syringe plunger head 132 needs to be retracted a relatively short distance, such vacuum force is negligible.

Once a two-way flow communication is established, a medicament or medicaments in the dispensing unit 110 and the plunger unit 112 are free to flow around the plunger head 132 in and out of both units. During this procedure, the closure element 108 remains in place in its sealed position.

By withdrawing the plunger head 132, together with bung 103, from the joining sleeve 125 and the dispensing unit body 102 respectively, the two compartments are now in communication with one another so that the contents of the two compartments can mix.

According to one embodiment of the invention, the withdrawal of plunger 130 is limited by a stopper element (not shown) on the plunger shaft 138. As the plunger 130 is withdrawn, the stopper element abuts against the shoulder 134 of closure element 108 and limits the travel of the plunger 130. Typically, the syringe assembly 100 would be shaken vigorously to mix the contents of the syringe assembly 100. The presence of the substantial portion of the plunger shaft 138 inside the plunger unit 112 enhances the mixing of the contents by functioning as an agitator during the shaking. This agitating function of the plunger shaft 138 may be further enhanced by providing vanes 131 in the portion of the plunger shaft that is positioned within the plunger unit 112.

When the contents of the syringe assembly 100 are completely mixed and the medicament is ready for dispensing, the syringe assembly 100 is oriented so that the dispensing unit is pointing downward. This will cause the medicament to drain into the dispensing unit 110. The volume of the two components of the medicament preferably is controlled so that the mixed medicament would fit completely inside the dispensing unit 110 without overflowing into the plunger unit 112. This minimizes any portion of the medicament from being wasted.

Figure 8:
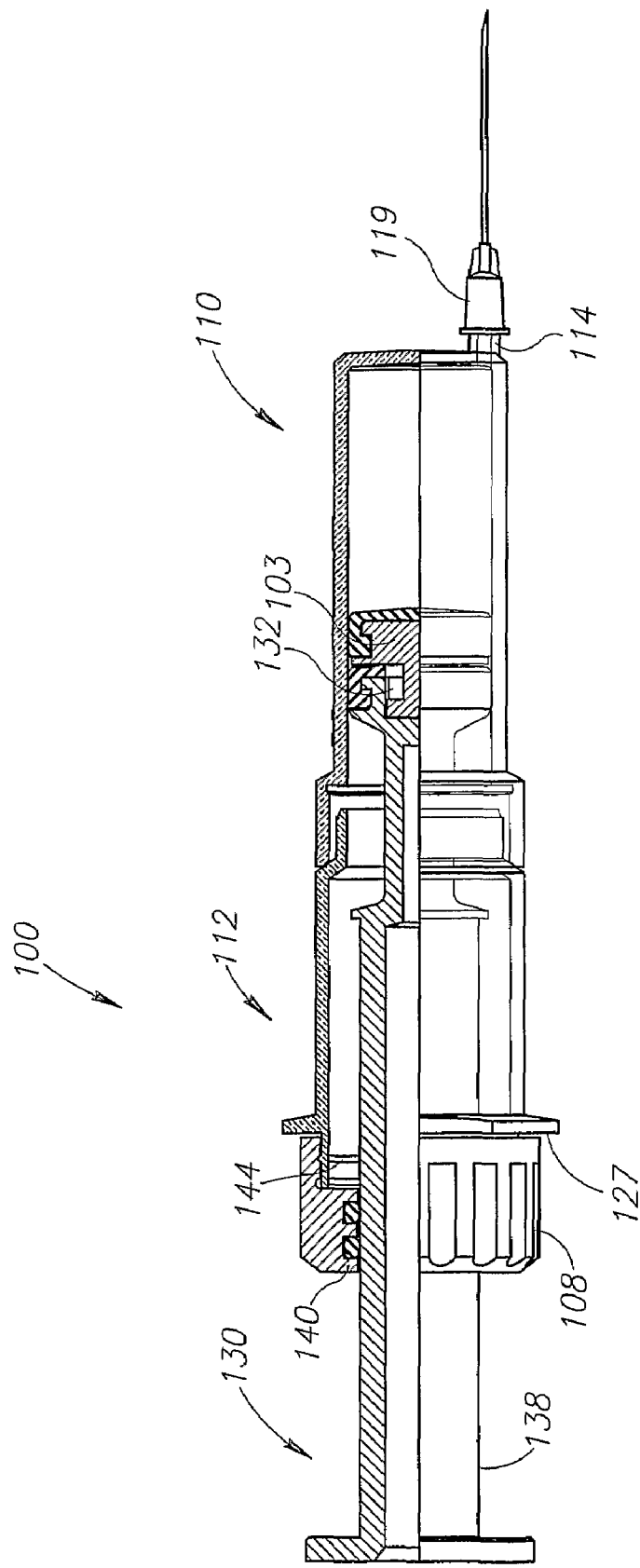
FIG. 8 is a partial sectional view of the syringe assembly of FIG. 7, where the plunger has been pushed into the dispensing unit for dispensing the mixed medicament, which is now in the dispensing unit.
Figure 9:
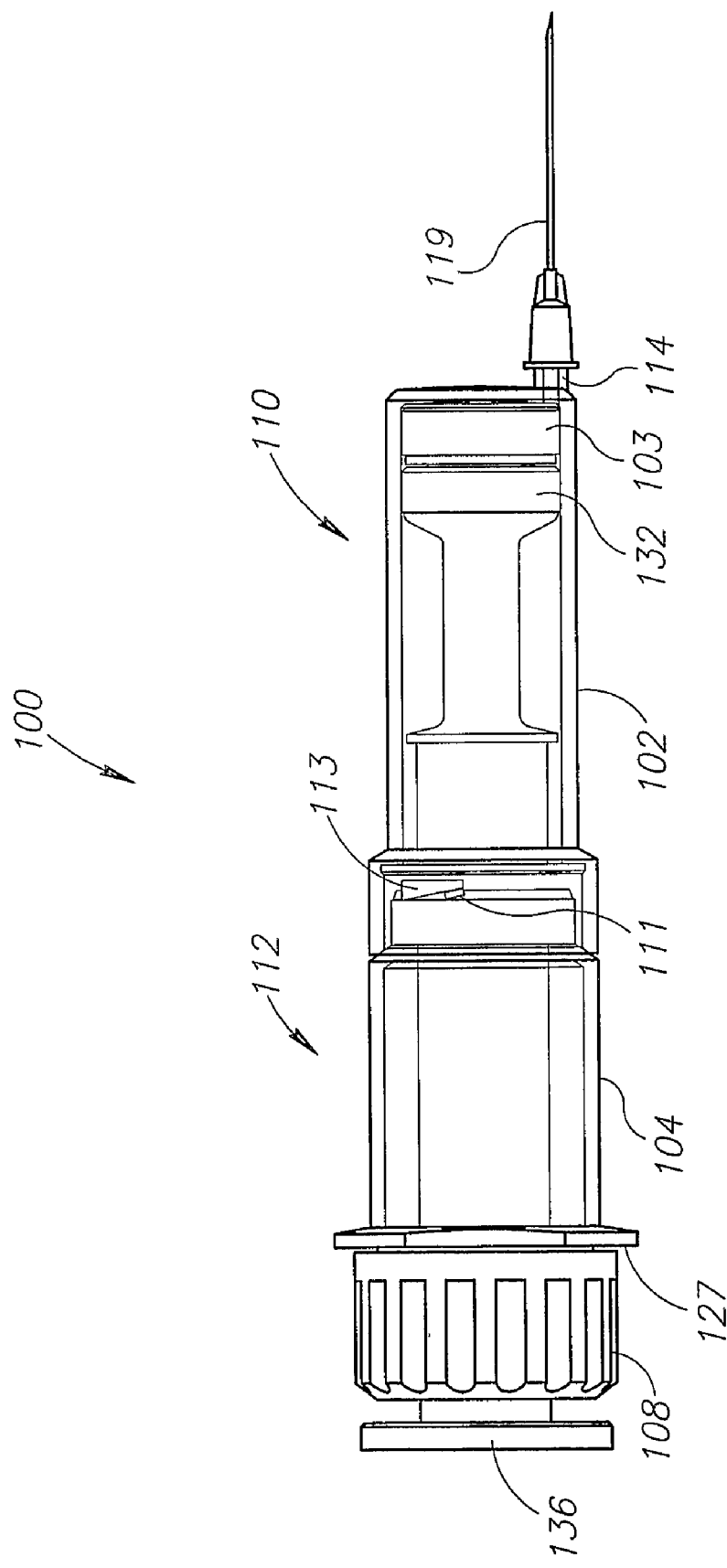
FIG. 9 is a perspective view of the syringe assembly of FIG. 7, where the plunger is in a fully depressed position after the medicament in the dispensing unit has been completely dispensed.

As seen in FIG. 8, the plunger 130 lockingly engaged to bung 103 is now pressed through joining sleeve 125 into the dispensing unit 110 for dispensing the mixed medicament, which is now in the dispensing unit. To completely dispense the medicament contained in the dispensing unit 120, the plunger 130 is fully depressed into the dispensing unit 110 as illustrated in FIG. 9.

Once the medicament has been dispensed, the needle 119 may be disposed of in any conventional manner, and the syringe assembly may also be discarded. Alternatively, the plunger unit 112 may be separated from the dispensing unit 110, by rotating so as to release the locking elements 111 and 113 from each other, and either or both units may be sterilized and re-used. It will be appreciated by those of ordinary skills in that art, that in order to depress 130 all the way from the plunger through the dispensing unit, air must enter the syringe assembly behind the axially moving plunger head 132. As will be further described herein below, shaft 138 is provided with a longitudinal groove allowing air from outside the syringe assembly to enter the plunger unit as the medicament is being displaced by the plunger head through joining sleeve 125 and body 102 of the dispensing unit. When this process takes place, the medicament is no longer present in body 104 of the plunger unit, thus it cannot leak out of the syringe assembly through the groove in shaft 138.

Figure 10A:
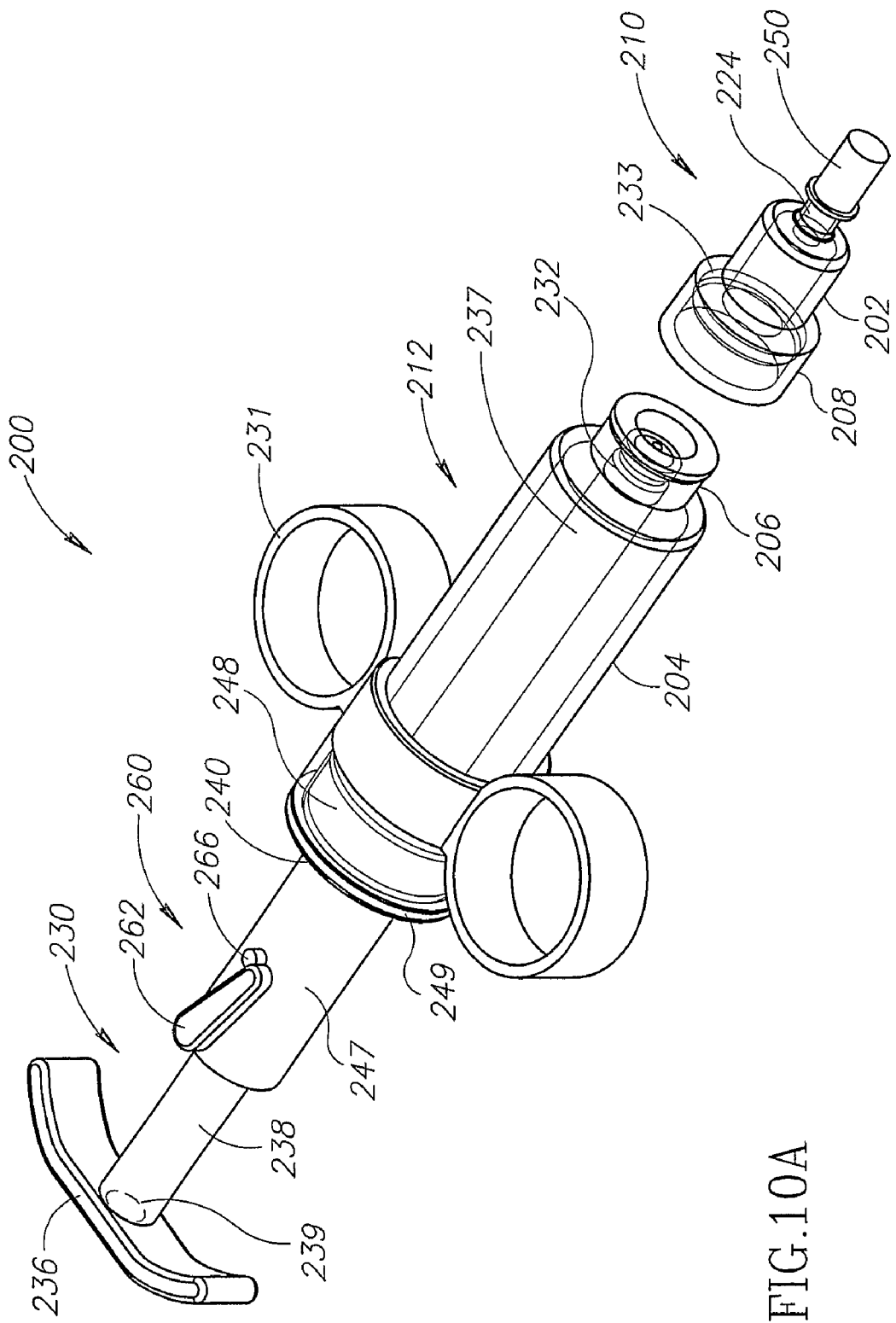
FIG. 10A is a perspective view of another embodiment of the syringe assembly of the invention in a non-assembled state, having two compartments particularly for use as a multi-dose syringe.
Figure 10B:
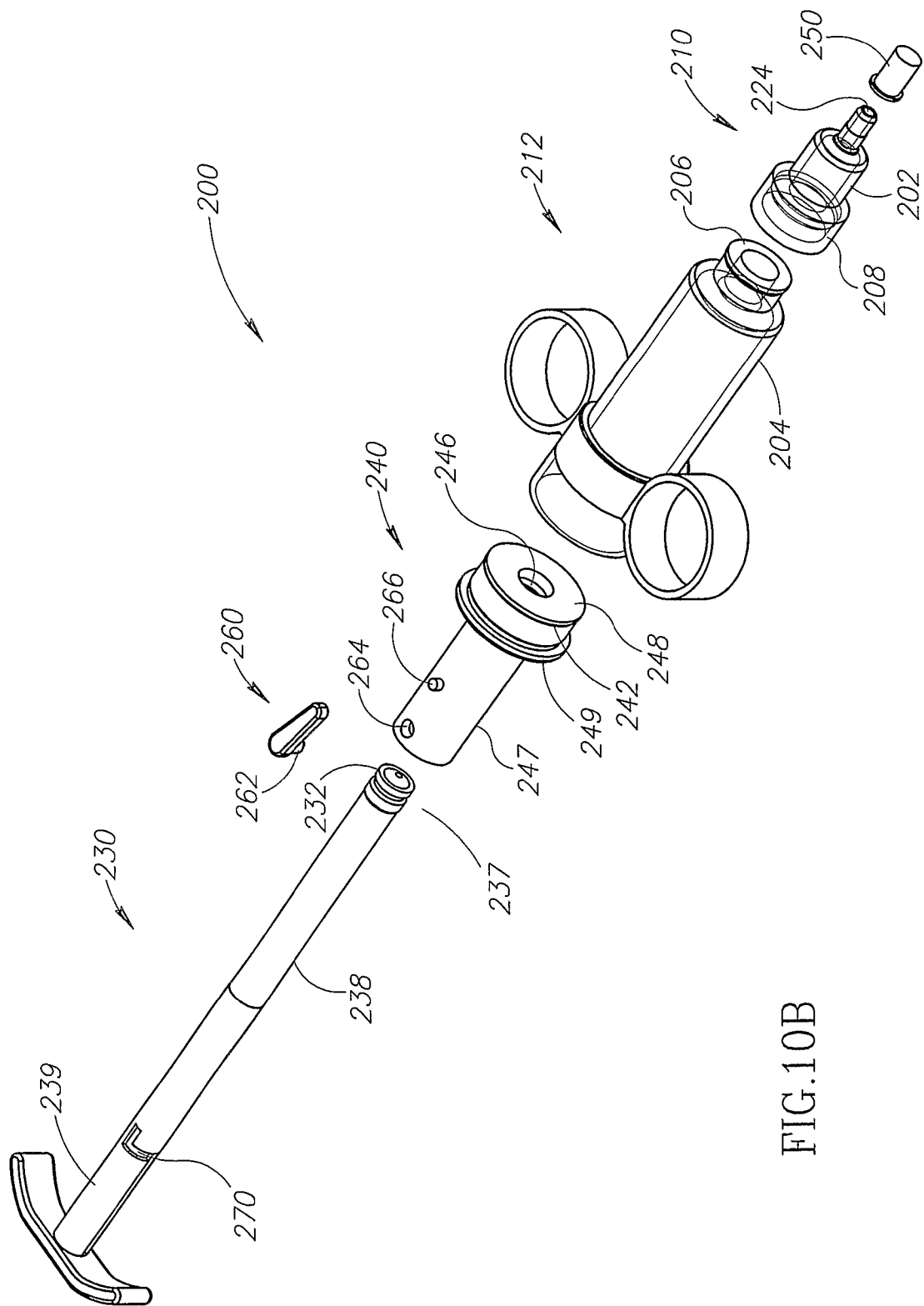
FIG. 10B is an exploded view of the syringe assembly of FIG. 10A.

FIGS. 10A and 10B illustrate another embodiment of a two-compartment syringe assembly particularly suited for providing multiple injections of a pre-selected dosage. This two-compartment syringe assembly 200 comprises a dispensing unit 210 having a substantially cylindrical body 202 including openings at top and bottom ends, and a plunger unit 212 having a substantially cylindrical body 204 including openings at top and bottom ends. Inner sidewall of body 202 having one diameter and inner sidewall body 204 having a larger diameter. The top-end opening of the plunger unit 212 defines a protruding neck serving as a joining sleeve 206 having inner sidewall of smaller diameter than the inner sidewall of plunger unit body 204. The bottom-end opening of the dispensing unit 210 defines a depending flange 208 sized to snugly engage the outer sidewall surface of the joining sleeve 206 of the plunger unit, thereby to join the two units together.

The syringe assembly 200 further comprises a plunger 230 having a plunger head 232 at its distal end 237. When the plunger 230 is inserted inside the plunger unit 212, the plunger head 232 sealingly engages the inner sidewall of joining sleeve 206 and seals the top-end opening of the plunger unit 212. A sealing washer 233 may be provided in the bottom-end opening of the dispensing unit 210 to provide a hermetic seal to prevent leakage between the dispensing unit 210 and the plunger unit 212. The plunger 230 may be provided with a thumb rest 236 near the proximal end 239 of the plunger shaft 238 that can also be used to withdraw the plunger 230 from the syringe. Such thumb rest 236 will be useful also when pressing the plunger 230 into the syringe. If desired, retaining rings 231 may be provided about plunger unit 212 for engagement by the fingers of the user during dispensing. A bottom closure member 240 for sealing the bottom end opening of the plunger unit 212 is also provided. Bottom closure member 240 is slidably mounted on the plunger 230 and is movable along plunger shaft 238 between the plunger's proximal end 239 and the bottom end opening of plunger unit body 204. The bottom closure member 240 is illustrated in detail in FIG. 10B. The bottom closure member 240 further comprises a base portion 247 and a radial flange 249 adjacent a bung portion 248.

The bottom closure member 240 has a central aperture 246 for slidably receiving the plunger shaft 238. The sidewall of the central aperture 246 is configured with at least one sealing rib (not shown) so that an appropriate seal is maintained at the interface between the plunger shaft 238 and the bottom closure member 240.

The bung portion 248 is sized to seat inside the bottom end of the plunger unit 212 and sealingly engage the plunger unit body 204 along its inner sidewall. The bung portion 248 is prevented from excess movement by radial flange 249, which is adapted to seat against the bottom open end of body 204. The bottom closure member 240 may be made of a single material or formed as a composite, but preferably at least the sealing ribs 242 and the bung portion 248 that sealingly engages the plunger unit body are made from an elastomer.

Preferably, a locking mechanism 260 is provided to prevent inadvertent movement of plunger 230 relative to the plunger unit 212. Locking mechanism 260 includes a pivotable screw 262 arranged to seat in a threaded aperture 264 in the base portion 247 of bottom closure member 240. A stopper pin 266 is affixed to the base 247 to limit the range of motion of pivotable screw 262. A step-shaped groove 270 is provided in the plunger shaft 238. Groove 270 extends longitudinally along shaft 238, turns 90 degrees and continues horizontally about the circumference of the shaft, and then turns again 90 degrees and extends lengthwise along another side of the shaft 238. Pivotable screw 262 seats in groove 270 and permits or prevents movement of the plunger, depending upon the depth to which it is screwed into the bottom closure member. Thus, when the pivotable screw 262 is screwed into the closure member, it presses against shaft 238, preventing its movement. When it is desired to withdraw or press the plunger, the pivotable screw 262 is unscrewed until it is stopped by stopper pin 266, which releases the pressure on the shaft and frees the screw within the aperture 264. The plunger shaft is now restricted to movement where the screw 262 slides along groove 270. Groove 270 also permits for air to enter the syringe when the plunger 230 is pressed so as to prevent vacuum from being created while plunger head 232 slides towards the top end opening of a nipple 224 of the dispensing unit.

Nipple 224 is preferably sealed with a removable closure. In this embodiment, nipple 224 is sealed with a screw cap 250. The screw cap is provided with screw threads (not shown) and nipple 224 is provided with mating threads so that the screw cap 250 can be screwed onto the nipple top-end opening.

The desired quality of the seals produced by the screw cap 250 and the bottom closure member 240 and sealing washer 233, will be dictated by the particular application for the syringe assembly such as the particular substance stored in each compartment of the syringe. For example, the seals may be hermetic or non-hermetic but liquid tight.

Alternatively, nipple 224 may be sealed with any other appropriate sealing methods. For example, nipple 224 may be heat sealed along its rim with a foil membrane made of an appropriate material that can be peeled away to dispense the contents of the syringe.

According to one embodiment of the invention, the bottom-end opening of dispensing unit 210 may also be sealed, either when the unit is empty to prevent contamination, or after being filled with a quantity of a component of a medicament.

According to a preferred embodiment, the dispensing unit 210 is not filled in advance, but has a pre-selected volume suitable for a single dosage of a medicament of which multiple, same dosages must be provided. It will be appreciated that dispensing unit 210 can be readily exchanged to provide any desired volume suitable for the required dosage.

All components of the syringe assembly 200 are preferably provided in sterile condition to prevent any contamination of the medicament or formulation to be stored in the syringe assembly 200. Of course, if required, the filling and assembly operation itself may be conducted in a sterile environment.

Figure 11A:
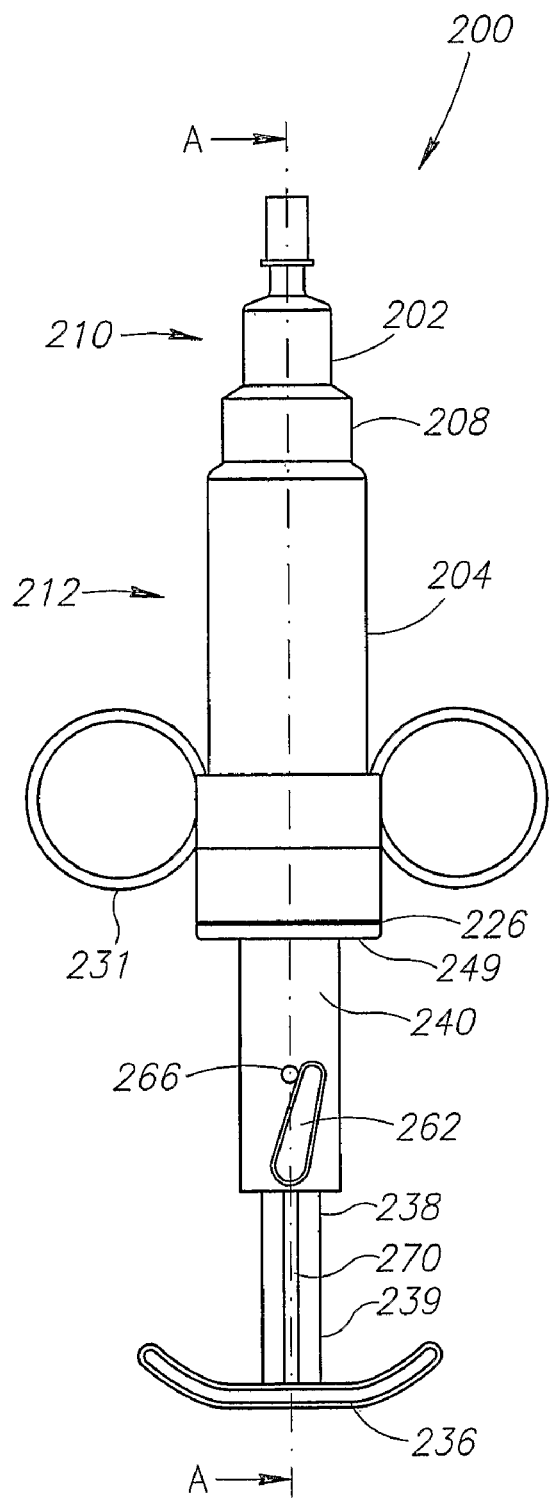
FIG. 11A is a plan view of the syringe assembly of FIG. 10 when the two compartments have been assembled to form a single syringe.

Next, FIGS. 11A-13 will be utilized to illustrate the process involved in filling the syringe assembly 200 for storage and also measuring a single pre-selected dose of the contents of the syringe assembly 200 and preparing it for dispensing. FIGS. 11A and 11B are respective plan and sectional view of the syringe assembly 200 when the plunger unit and the dispensing unit have been assembled to form a single syringe assembly. It will be appreciated that, for a multi-dose syringe, the plunger unit 212 will be able to hold a relatively large volume of medicament, for example 10 cc, while the dispensing unit 210 will hold only a single, preferably precisely-measured dose, of say 1 cc.

Figure 11B:
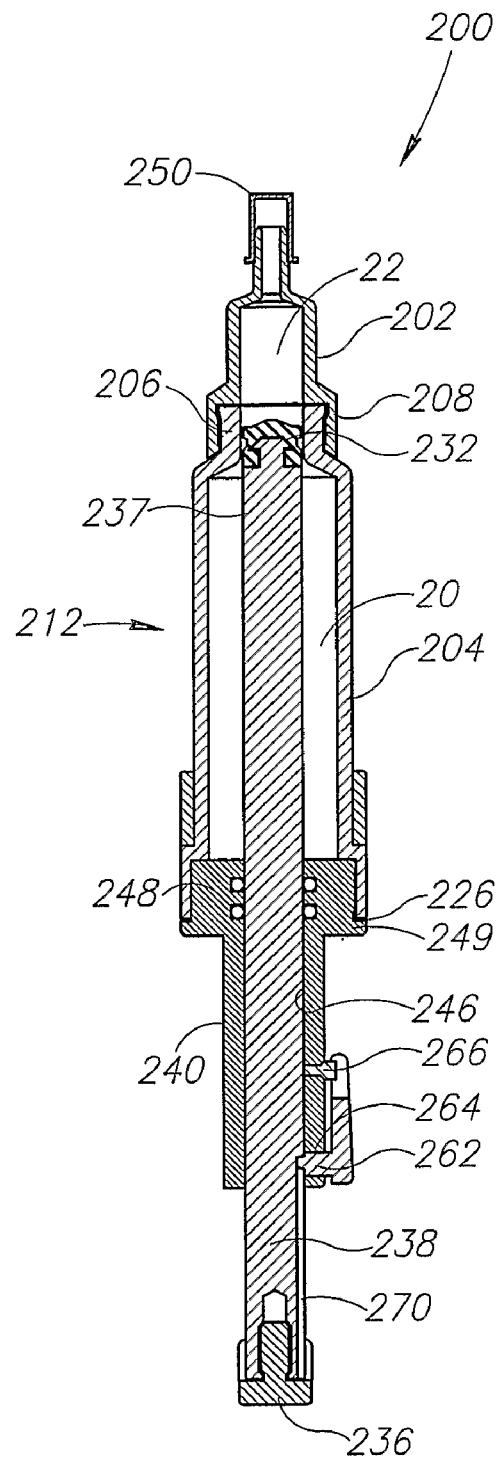
FIG. 11B is a sectional view of the syringe assembly of FIG. 11A taken along line A-A.

In FIGS. 11A and 11B, a medicament 20 introduced into the plunger unit 212 is a liquid. The bottom closure member 240 is removed from the bottom-end opening 226 of plunger unit 212 to its unsealed position (if not already in its unsealed position) and may be positioned near the proximal end 239 of the plunger 230 to facilitate the filling of the plunger unit 212.

Next, the plunger unit 212 is filled with a medicament 20 through the bottom opening 226. During this process, the plunger 230 is maintained in its position so that the plunger head 232 remains engaged with the joining sleeve 206 of body 204, confining the medicament 20 within the plunger unit 212.

After a desired amount of the medicament 20 is introduced into the plunger unit 212, the bottom opening 226 is sealed by sliding the bottom closure member 240 along the plunger shaft 238 towards its distal end 237 and snap-fitting the bottom closure member 240 onto the bottom-end opening of plunger unit 212. FIG. 11B illustrates the syringe assembly 200 after the bottom closure member 240 has been fitted into its sealed position. The medicament 20 is kept in the compartment within the plunger unit 212 and may be stored until ready to be measured and dispensed. It will be appreciated that the locking mechanism 260 is in the locking configuration, where pivotable screw 262 engages groove 270 in the plunger shaft 238.

Figure 12:
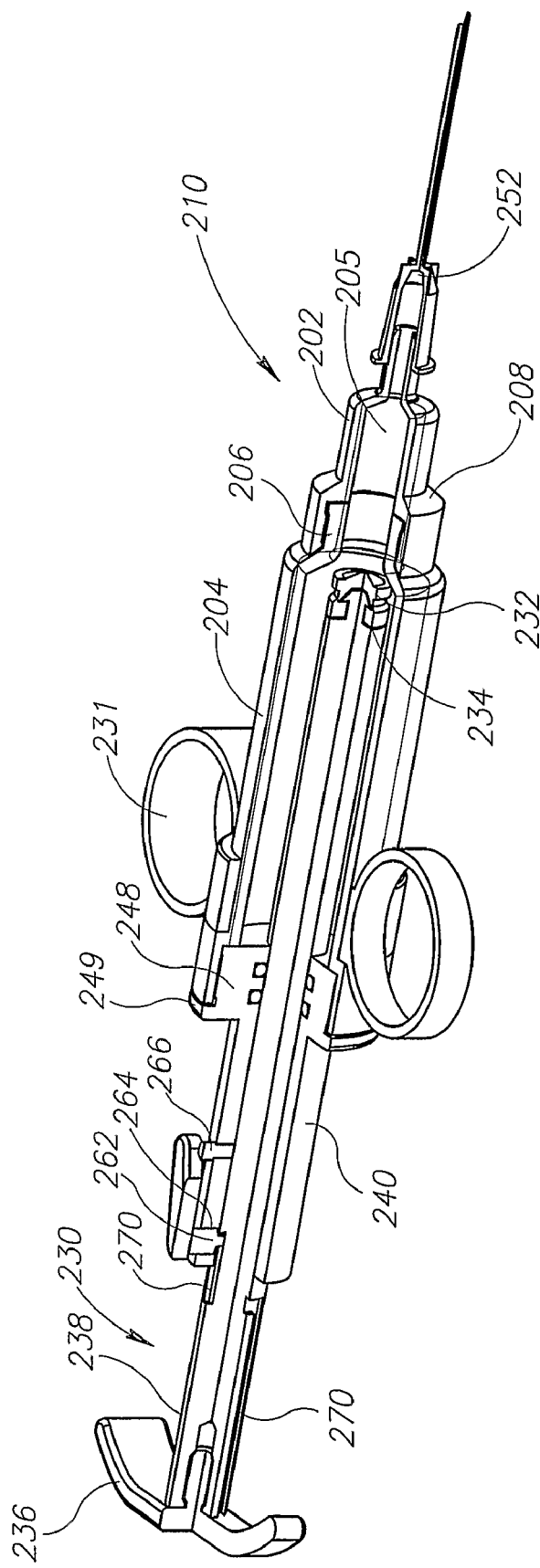
FIG. 12 is a partially cut away perspective view of the syringe assembly of FIG. 11A, where the plunger has been withdrawn to permit flow communication between the plunger unit and the dispensing unit.

FIG. 12 is a partially cut away illustration of the syringe assembly 200 in a configuration where flow communication exists between the plunger unit and the dispensing unit. The plunger 230 has been withdrawn so that the plunger head 232 is no longer sealingly engaging joining sleeve 206 but lies within the plunger unit 212. The plunger 230 may be provided with stopper tabs 234 that limit the travel of the plunger 230 when it is being withdrawn to prevent any compromise of the seal between the plunger shaft 238 and the bottom closure member 240. Because the inner sidewall of plunger unit body 204 is of a larger diameter than the outer diameter of plunger head 232, dispensing unit 210 and plunger unit 212 are in flow communication with one another. In this way, medicament 20 flows into and fills the pre-sized compartment 205 in dispensing unit body 202.

To dispense a single dose of the medicament, the syringe assembly 200 is placed in an orientation illustrated in FIG. 12 with its dispensing end pointing down and the plunger end pointing up. This causes the medicament (not shown) to completely fill compartment 205 in the dispensing unit 210. The plunger head 232 is then pressed back into joining sleeve 206, thereby sealing a single dosage in the dispensing unit 210, and the syringe assembly 200 may be used to administer the dosage like a standard syringe. Prior to administering of the dosage, the user may position the syringe assembly 200 in a top end up orientation for allowing any air trapped in the dispensing unit 210 to rise. The screw cap 250 (see FIG. 11B) may then be removed to attach an appropriate dispensing device to the top end of the syringe assembly 200. For example, a hypodermic needle 252 may be attached to the syringe assembly 200 at the top end, as shown in FIG. 12. Once an appropriate dispensing device is attached, the plunger 230 is pressed further into syringe body 202.

Figure 13:
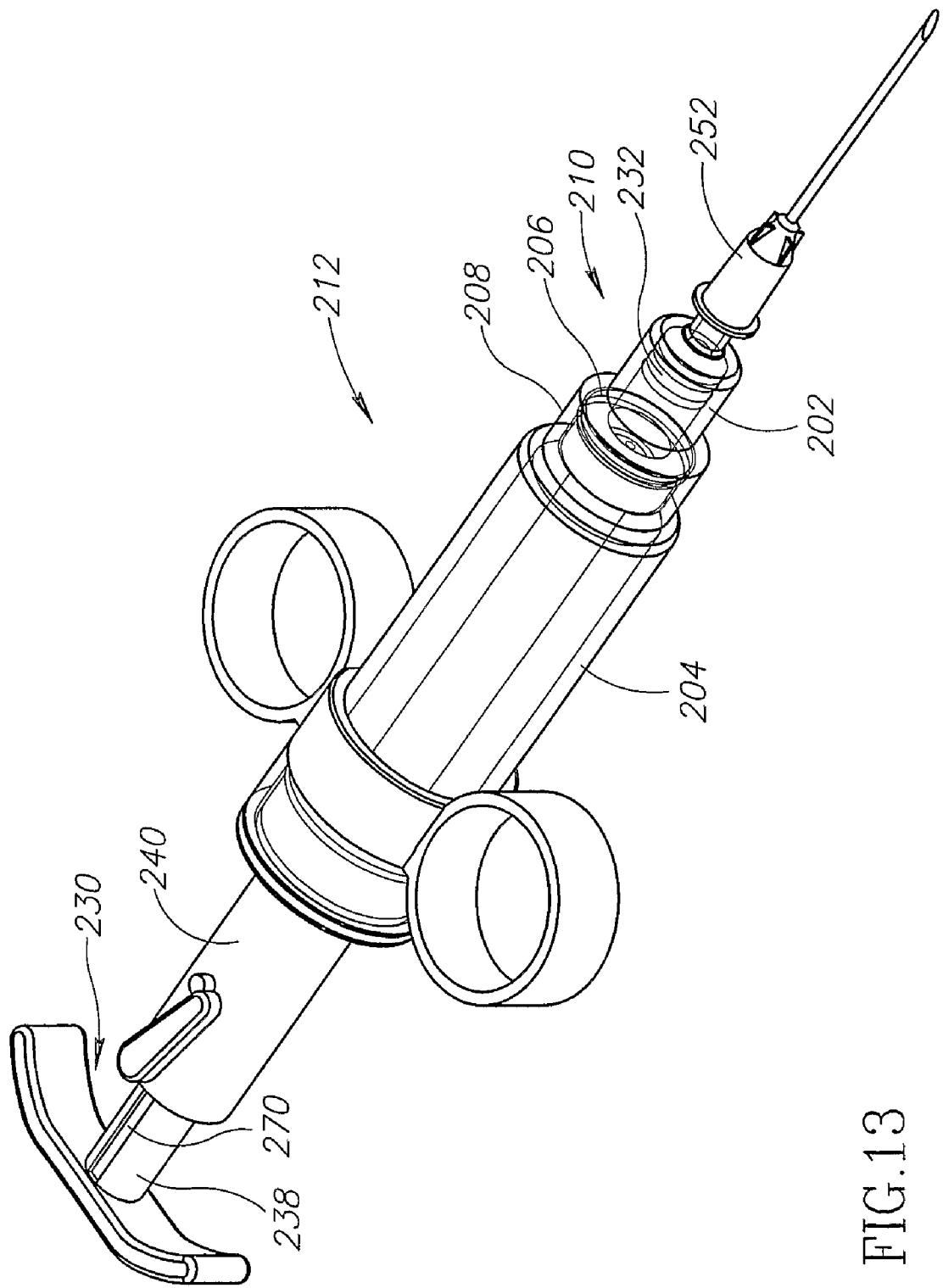
FIG. 13 is a perspective view of the syringe assembly of FIG. 11A, where the plunger is in a fully depressed position after the dose of the medicament in the dispensing unit has been completely dispensed.

FIG. 13 is a perspective view of the syringe assembly of FIG. 10, where plunger 230 is in a fully depressed position after the medicament in the dispensing unit has been completely dispensed. As the plunger head 232 advances further into the dispensing unit 210, the increase in the volume of the plunger unit 212 will create a low pressure condition in the plunger unit 212 and may interfere with the dispensing process. To alleviate this concern, groove 270 on plunger shaft 238 provides an air vent channel. As the plunger advances farther into the dispensing unit 210, groove 270 will break the seal between the bottom closure member 240 and the plunger shaft 238 and allow outside air to vent into the plunger unit 212.

Figure 14:
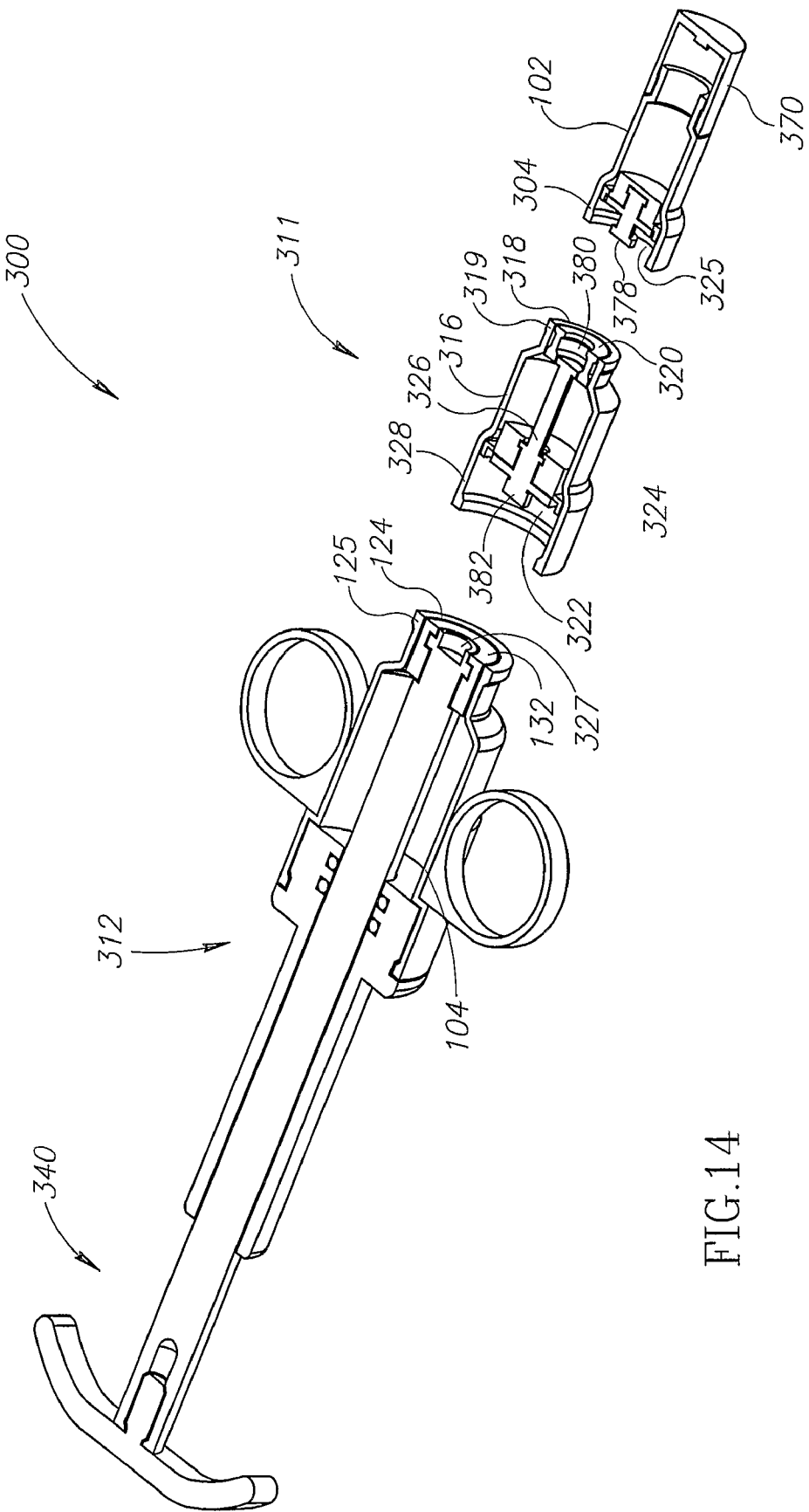
FIG. 14 is a perspective view of an embodiment of the syringe assembly of the invention in a non-assembled state, having three compartments where the syringe separate units are illustrated as being translucent in order to show the internal structures of each of the units of the syringe.
Figure 15:
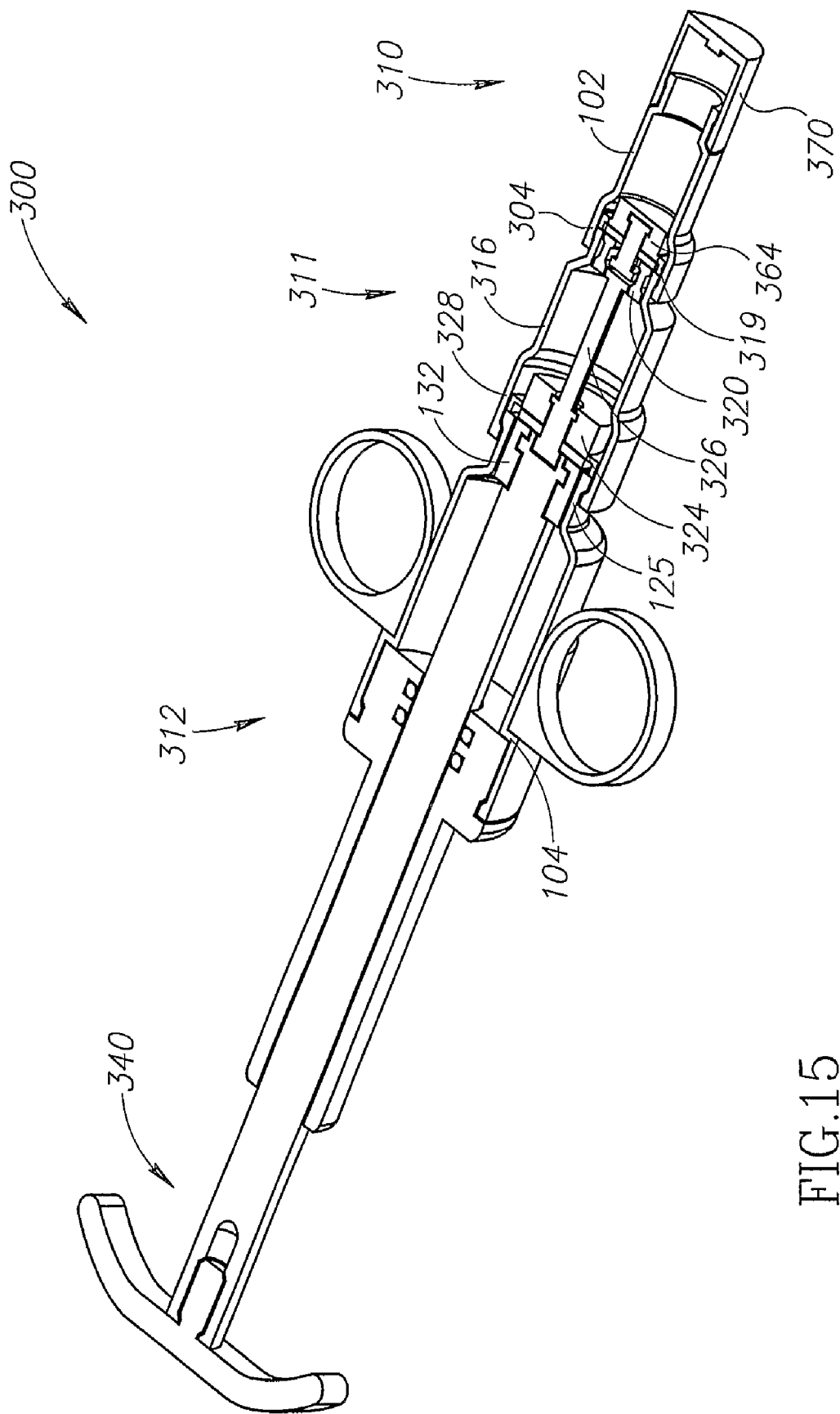
FIG. 15 is a partial sectional view of the assembled syringe assembly of FIG. 14, where the plunger is in the sealed position.
Figure 16:
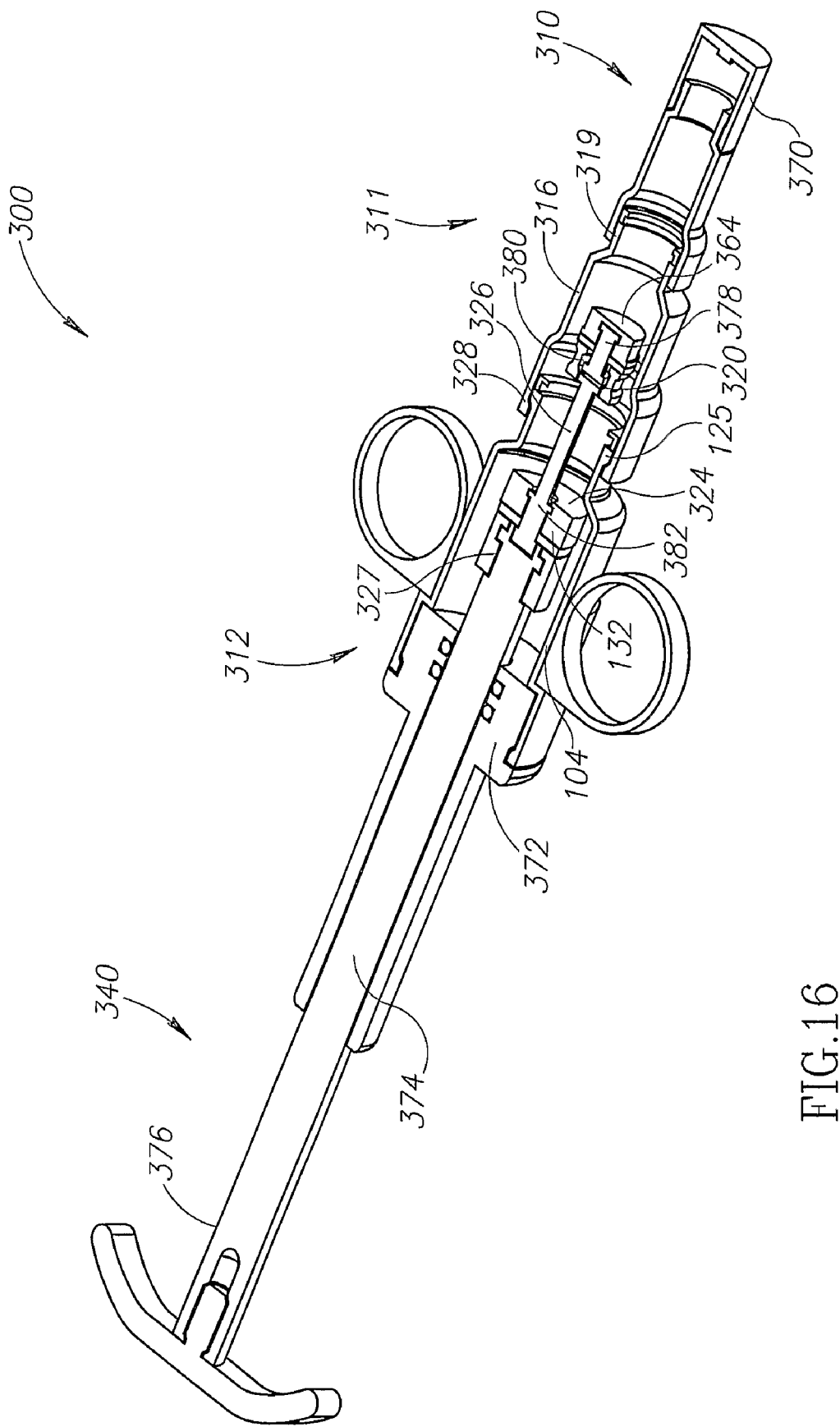
FIG. 16 is a partial sectional view of the assembled syringe assembly of FIG. 14, where the plunger has been withdrawn so that the plunger head and the second extension bung are in the plunger unit and the first extension bung is in the extension unit, so that the three compartments are in communication with one another allowing the contents of the three compartments to mix.

FIGS. 14-16 illustrate another embodiment of the invention, a syringe assembly 300 having three separate units for separately storing up to three different components of a medicament or a formulation, each in separate compartments until ready for use, wherein the components may be mixed to form the medicament. The syringe assembly 300 has three units—a plunger unit 312, a dispensing unit 310, and an extension unit 311 adapted to be affixed between the dispensing unit and the plunger unit.

The syringe assembly 300 has three main body sections, a dispensing unit body 102, an extension unit body 316, and a plunger unit body 104, with the inner sidewall diameter of the syringe body increasing progressively with each section. In other words, the inner sidewall diameter of the plunger unit body 104 is larger than the inner sidewall diameter of extension unit body 316, which, in turn, is larger than the inner sidewall diameter of the dispensing unit body 102.

The dispensing unit 310 is substantially similar to dispensing unit 110 of FIG. 1, and the plunger unit 312 is substantially similar to plunger unit 112 of FIG. 1, so they will not be described in detail again, rather like elements have like reference numerals.

Extension unit 311 has two open ends: a top-end opening of body 316 defining a neck portion having an inner sidewall diameter smaller than the inner sidewall diameter of body 316, and forming a joining sleeve 319, having a top-end opening 318; and a bottom-end opening of body 316 defining a depending flange portion 328 having a bottom-end opening 322. Joining sleeve 319 is adapted and configured to sealingly seat within a depending flange portion 304 of dispensing unit 310, and snuggly fit its outer sidewall, while joining sleeve 125 is adapted and configured to sealingly seat within depending flange portion 328 of extension unit 311, and snuggly fit its outer sidewall, thus assembling the syringe assembly. A sealing element (not shown) is disposed in an upper portion of each of flange portion 304 and depending flange portion 328, for engagement by a top edge of said joining sleeve to provide hermetic seals between the dispensing unit and the extension unit and the plunger unit, respectively.

Extension unit 311 includes a substantially cylindrical body 316, having a sealable opening at each end. A first extension bung 320 is positioned in joining sleeve 319 of the extension unit 311 adjacent the dispensing unit, for a sealing engagement with inner sidewall of a joining sleeve 319. A second extension bung 324 is positioned in body 316 at the bottom end opening 322 of extension unit 311 adjacent the plunger unit, for sealing engagement with inner sidewall of body 316. First extension bung 320 is adapted and configured to be affixed to a bung 364 positioned in body 102 of the dispensing unit 310, for a sealing engagement with inner sidewall of body 102. Second extension bung 324 is adapted and configured to be affixed to a plunger head 132 positioned in body 104 of the plunger unit 312, for a sealing engagement with inner sidewall of joining sleeve 125. A connecting rod 326 couples the first extension bung 320 with the second extension bung 324 to permit them to slide in tandem inside the syringe assembly.

Bung 364 at the bottom end opening of dispensing unit 310 is adapted and configured to sealingly engage body 102 and seal the bottom end opening 325 of the dispensing unit compartment. Bung 364 includes a locking member 378. Bung 320 includes a matching opening 380, complementary to the locking member 378 of bung 364 for a locking engagement. Similarly, bung 324 at the bottom end opening of extension unit 316 is adapted and configured to sealingly engage body 316 and seal the bottom end opening 322 of the extension unit compartment. Bung 324 includes a locking member 382. Joining sleeve 125 of top-end opening 124 of plunger unit 312 is sealed by plunger head 132, adapted and configured to sealingly engage body 104 and seal the plunger unit compartment. Plunger head 132 includes a matching opening 327 complementary to the locking member 382 of bung 324 for a locking engagement. Joining sleeve 125 further includes at least two slightly slanted, peripherally extending ribs (not shown in FIGS. 14-16 but are substantially the same as extending ribs 33 shown in FIG. 1) configured for locking engagement with at least two matching ribs (not shown in FIG. 14 but is substantially the same as matching ribs 36 shown in FIG. 1) peripherally extending from the inner sidewall of flange portion 328 of extension unit 311. In a similar fashion, joining sleeve 319 of body 316 of extension unit 311 includes at least two slightly slanted, peripherally extending ribs (not shown) configured for locking engagement with at least two matching ribs (not shown) peripherally extending from the inner sidewall of depending flange portion 304 of dispensing unit 310.

FIG. 15 is a cutaway illustration of the fully assembled syringe assembly 300 in a ready-for-storage configuration. Plunger 340 is positioned inside body 104 of plunger unit 312, so that plunger head 132 sealingly engages the inner sidewall of joining sleeve 125, and lockingly engages second extension bung 324. Bung 324 sealingly engages the inner sidewall of body 316 of extension unit 311. First extension bung 320 sealingly engages the inner sidewall of joining sleeve 319 of extension unit 311, and lockingly engages bung 364 which in turn sealingly engages the inner sidewall of body 102 of dispensing unit 310. In this storage configuration, plunger head 132 and lockingly engaged second extension bung 324 form a partition between the compartment in plunger unit 312 and the compartment in extension unit 311, while first extension bung 320 and lockingly engaged bung 364 form a partition between the compartment in extension unit 311 and the compartment in dispensing unit 310. The seal formed by the plunger head 132 in joining sleeve 125 is hermetic so that the component stored in the compartment of plunger unit 312 and the component stored in the compartment of extension unit 311 may be kept separate until ready to be mixed. The seal formed by the second extension bung 320 in joining sleeve 319 serves the same function between the compartment of extension unit 311 and the compartment of dispensing unit 310.

First extension bung 320 is preferably made from elastomer and may have a composite structure including seal forming portions, i.e., sealing ribs (not shown) made from one or more elastomers. The rest of bung 320 may be made from any material suitable to maintain the structural shape of bung 320 and chemically compatible with the elastomer portions. The diameter of bottom portion 369 of bung 320 is substantially the same as the diameter of joining sleeve 319 and body 102 of dispensing unit 310 so that bung 320 can be moved through dispensing unit 310 to form a seal with the inside surface of the compartment in body 102.

Second extension bung 324 is positioned within body 316 sealing the bottom-end opening of extension unit 311. Second bung 324 is coupled to plunger head 132 to permit them to slide in tandem inside the syringe assembly.

The process of filling and assembling the syringe assembly 300 will is now described. Plunger unit 312 and dispensing unit 310 shown in FIGS. 14 and 15 may be separately filled substantially in the same manner as plunger unit 112 and dispensing unit 110 of FIGS. 5 and 6 may be separately filled, as described in detail above. Thus, the process of filling them will not be described in detail again.

To separately fill extension unit 311 shown in FIG. 14, first extension bung 320 coupled to connecting rod 326 is positioned inside joining sleeve 319 of the extension unit 311, and first extension bung 320 seals top-end opening 318 of extension unit 311. The compartment defined by extension unit body 316 may be filled with a component of a formulation through sealable filling opening 322 on the bottom side of the extension unit. Sealable filling opening 322 may then be sealed by second extension bung 324.

Alternatively, the compartment defined by extension unit body 316 may be more conveniently filled by sealing top end opening 318 with a foil or a non-metallic membrane having a single or multi-layered structure. The extension unit may now be rotated through 180 degrees and filled through the sealable bottom end opening 322. First extension bung 320 and second extension bung 324 coupled by connecting rod 326 may now be positioned inside the extension unit body 316 whereby the bottom-end opening of the extension unit is sealed by second extension bung 324.

It will be appreciated that the dispensing unit, extension unit, and plunger unit of the invention may be separately filled with different components and in different locations, and can be sealed and stored separately prior to assembly and use.

Syringe assembly 300 as illustrated in FIGS. 14 and 15 consists of three completely sealed compartments—the dispensing unit 310, the extension unit 311m and the plunger unit 312—where each compartment may be holding a component of a medicament, coupled together. The coupling of the three units, according to the illustrated embodiment, is as follows. A sealing washer (not shown) is disposed in depending flange 328. Joining sleeve 125 of the plunger unit 312 is inserted into depending flange 328 of extension unit 311. At the same time, locking member 382 on second extension bung 324 engages the matching opening 327 in plunger head 132. The extension unit is then rotated relative to the plunger unit, in order to sealingly couple these two separate units. Similarly, a sealing washer (not shown) is disposed in depending flange 304 of dispensing unit 310. Joining sleeve 319 of extension unit 311 is inserted into depending flange 304 of dispensing unit 310. At the same time, locking member 378 on bung 364 engages the matching opening 380 in bung 320. The dispensing unit is then rotated relative to the plunger unit and extension unit already sealingly coupled to each other, in order to sealingly couple the dispensing unit to the other two units of the syringe assembly. It will be appreciated that syringe assembly 300 may be assembled in a substantially similar fashion starting from sealingly coupling the extension and dispensing units.

Peripherally, extending ribs (not shown in FIGS. 14-16) on joining sleeve 125 of the plunger unit 312 (for example, as illustrated in FIG. 6) have been rotated to engage two matching ribs peripherally extending from the inner sidewall of depending flange portion 328 of the extension unit 311 (not shown in FIGS. 14-16). In a substantially similar fashion, peripherally extending ribs (not shown in FIGS. 14-16) on joining sleeve 319 of extension unit 311 (for example, as illustrated in FIG. 6) have been rotated to engage two matching ribs peripherally extending from the inner sidewall of depending flange portion 304 of dispensing unit 310 (not shown in FIGS. 14-16).

In the embodiment where the bottom end opening of the dispensing unit is sealed by a membrane or laminate, assembly of the assembling of the syringe assembly is accomplished by removing the seal from the bottom end of the dispensing unit, when in an upside down position, and locking the extension unit and the dispensing unit together, as described above. Bung 320 positioned inside joining sleeve 319 provides a seal between the two compartments of the extension and dispensing units of the syringe assembly, preventing flow communication between these two units until ready for dispensing.

Then, a cap 370 may be removed and a syringe needle (not shown) may be attached to the top-end opening of dispensing unit 310. Depending on the application, other dispensing apparatus may be attached to the top-end opening to dispense the medicament or any other formulation.

The process involved in preparing and dispensing the medicament from the two components stored in the syringe assembly 300 will now be described with reference to FIGS. 14-16. In order to mix the three components of a medicament stored in the syringe assembly 300, the plunger 340 lockingly coupled to second bung 324 which in turn is coupled to first extension bung 320 via connecting rod 326, which in turn is lockingly coupled to bung 364, is first drawn back towards the proximal end 376 of the plunger 340, so that the plunger head 132 disengages from the joining sleeve 125, second extension bung 324 disengages from body 316, first extension bung 320 disengages from joining sleeve 319, and bung 364 disengages from body 102, simultaneously, as illustrated in FIG. 16. It will be appreciated that withdrawing the plunger 340 moves both plunger head 132 and lockingly coupled second extension bung 324 into the plunger unit whose body 104 has an inner sidewall diameter larger than the joining sleeve 125 and body 316 of the extension unit in which they were sealingly seated, respectively, thereby permitting a two-way flow communication between the plunger unit and the extension unit. Simultaneously, both first extension bung 320 and lockingly coupled bung 364 move into the extension unit whose body 316 has an inner sidewall diameter larger than the joining sleeve 319 and the body 102 of the dispensing unit, in which they were sealingly seated, thereby permitting a two-way flow communication between the extension unit and the dispensing unit. Thus, a component or components of a medicament in the dispensing unit 310, the extension unit 311, and the plunger unit 310 are now free to flow around the plunger head 132 coupled to second extension bang 324, and first extension bung 320 coupled to bung 364, in the assembled syringe. During this procedure, closure element 372 shown in FIG. 16 as a bung remains in place in its sealed position.

Thus, by withdrawing the plunger 340, the three compartments have come into two-way flow communication with one another so that the contents of the three compartments can mix.

Typically, the syringe assembly 300 would be shaken vigorously to mix the contents of the syringe assembly 300. The presence of a substantial portion of plunger shaft 374 inside the plunger unit 312 and a substantial portion of connecting rod 326 inside the extension unit 311 enhances the mixing of the contents by functioning as agitators during the shaking. This agitating function of plunger shaft 374 and connecting rod 326 may be further enhanced by providing vanes (not shown) in the portions of the plunger shaft that is positioned within the plunger unit and the connecting rod that is positioned within the extension unit.

Once the contents of the syringe assembly 300 are completely mixed and the medicament is ready for dispensing, the syringe assembly 300 is oriented so that the dispensing unit is pointing downward. This will cause the medicament to drain into the dispensing unit 310. The volume of the three components of the medicament preferably is controlled so that the mixed medicament would fit completely inside the dispensing unit 310 without overflowing. This minimizes any portion of the medicament from being wasted.

Next, while maintaining the dispensing unit oriented downwardly, the plunger 340 is pushed down until first extension bung 320 sealingly engages body 102 of dispensing unit 310. The syringe assembly 300 then may be turned into the orientation with the top end of the syringe assembly pointing upwardly. Then, cap 370 may be removed and a hypodermic needle (not shown) may be attached to the top-end opening of dispensing unit 310. In this configuration, the syringe assembly 300 operates similarly to a standard syringe. To completely dispense the medicament contained in the dispensing unit 310, the plunger 340 is fully depressed into the syringe assembly 300. It would be apparent to one of ordinary skill in the art that the syringe assembly 300 may be provided with a dispensing apparatus other than a hypodermic needle for dispensing the medicament or any other solution.

It will further be appreciated by, that more than one extension unit may be utilized to assemble a syringe assembly of a desired number of compartments.

Figure 17:
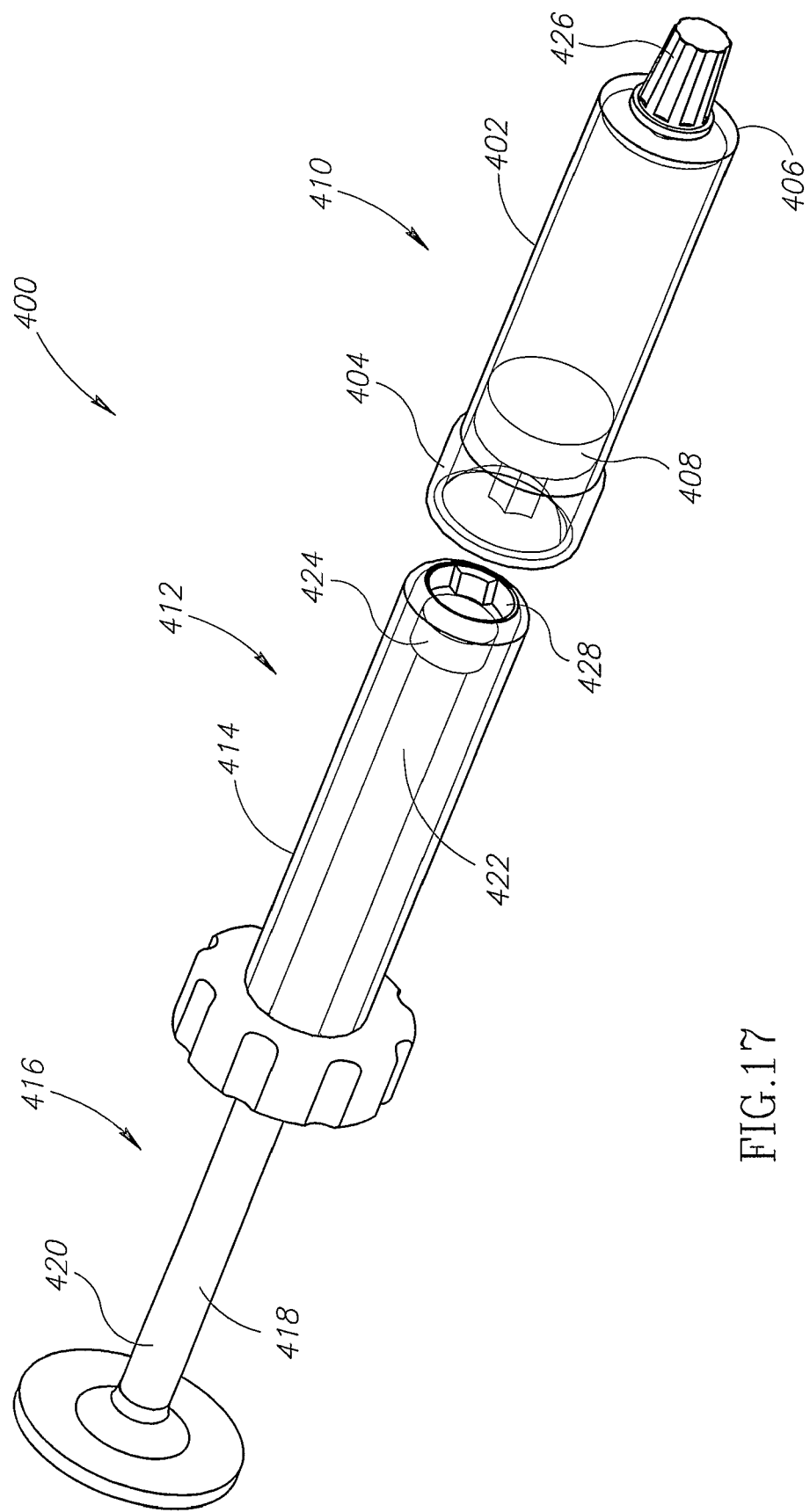
FIG. 17 is a perspective view of another embodiment of the syringe assembly of the invention in a non-assembled state.

Referring now to FIG. 17 there is shown according to another embodiment of the invention a two-unit syringe assembly 400 in a non-assembled state, including a dispensing unit 410 including a body 402 having bottom and top end sealable openings. Preferably, body 402 is substantially cylindrical. The bottom portion of body 402 may define a depending flange 404 adapted and configured for a locking engagement with a plunger unit 412. Bottom end opening of body 402 may be adapted and configured for a sealing engagement with a bung 408.

The top portion of body 402 may define an open ended nipple 406 with a top-end opening. Nipple 406 may be adapted and configured for attaching an appropriate dispensing device, e.g. a hypodermic needle (not shown). Since dispensing unit 410 is substantially similar to dispensing unit 110 of FIG. 1, it will not be described in detail again.

Syringe assembly 400 further includes a plunger unit 412 which is engaged with dispensing unit 410 to form a two-unit syringe assembly. Plunger unit 412 has a body 414. Preferably, body 414 is substantially cylindrical. Plunger unit 412 also includes a plunger 416. Once plunger and dispensing units are assembled, plunger 416 may be axially displaced in the syringe assembly. Plunger 416 consists of a user manipulable plunger shaft 418, having a proximal end 420 and a distal end 422 and is provided with a substantially cylindrical plunger head 424 at distal end 422. It is a particular feature of this embodiment of the invention that plunger unit 412 is adapted and configured for holding only plunger 416 and allowing it to axially move through the syringe assembly, and does not contain a component or formulation for mixing or dispensing. Thus, plunger unit 412 need not be sealed and plunger head 424 need not engage sealingly the inner sidewall of body 414 or the inner sidewall of body 402, as in other embodiments of the invention described herein above.

Bung 408 is adapted and configured for a sealing engagement with the inner sidewall of dispensing unit body 402 in a fluid-tight manner, forming a hermetically sealed partition between dispensing unit 410 and plunger unit 412. It will be appreciated that sealing bung 408 is configured and adapted for sliding engagement with the inner sidewall of dispensing unit body 402, and slides therealong during dispensing of the contents of the dispensing unit, while maintaining the seal. Also, bung 408 and plunger head 424, and dispensing unit 410 and plunger unit 412 are adapted and configured for a locking engagement with one another, respectively, during the assembly procedure, in the same fashion as described herein above. The upper portion of the plunger unit body 414 functions like the joining sleeve 34 in FIG. 1 described above, and lockingly engages the depending flange 404 of the dispensing unit.

According to another particular feature of the embodiment described in FIG. 17, the inner sidewall diameter of plunger unit body 414 is smaller than the inner sidewall diameter of dispensing unit body 404. Thus, when the syringe is assembled, plunger head 424 can move into dispensing unit body 402 during the dispensing procedure, but bung 408 cannot move into plunger unit body 414 when plunger 416 is retracted by the user. One advantage of the syringe assembly according to this embodiment of the invention is that the medicament may be hermetically stored in the dispensing unit very much like in an ampoule as known, then just prior to use the plunger and dispensing units are assembled, cap 426 is removed, a hypodermic needle (not shown) is coupled to nipple 406, and the syringe assembly is ready for action. This procedure is a fast and efficient way to administer a medicament as it eliminates the need to first draw the medicament from the ampoule into the syringe before dispensing. Another advantage of the syringe assembly according to this embodiment is that the plunger unit can be used repeatedly for dispensing a medicament or a solution from any number of dispensing units without the need to clean or sterilize it before each use. Another advantage is that, as manufacturing of a dispensing unit is cheaper than manufacturing of a plunger unit, the use of only one plunger unit for dispensing the medicament or the solution from a large number of dispensing units significantly reduces the costs of administering medicaments.

Figure 18:
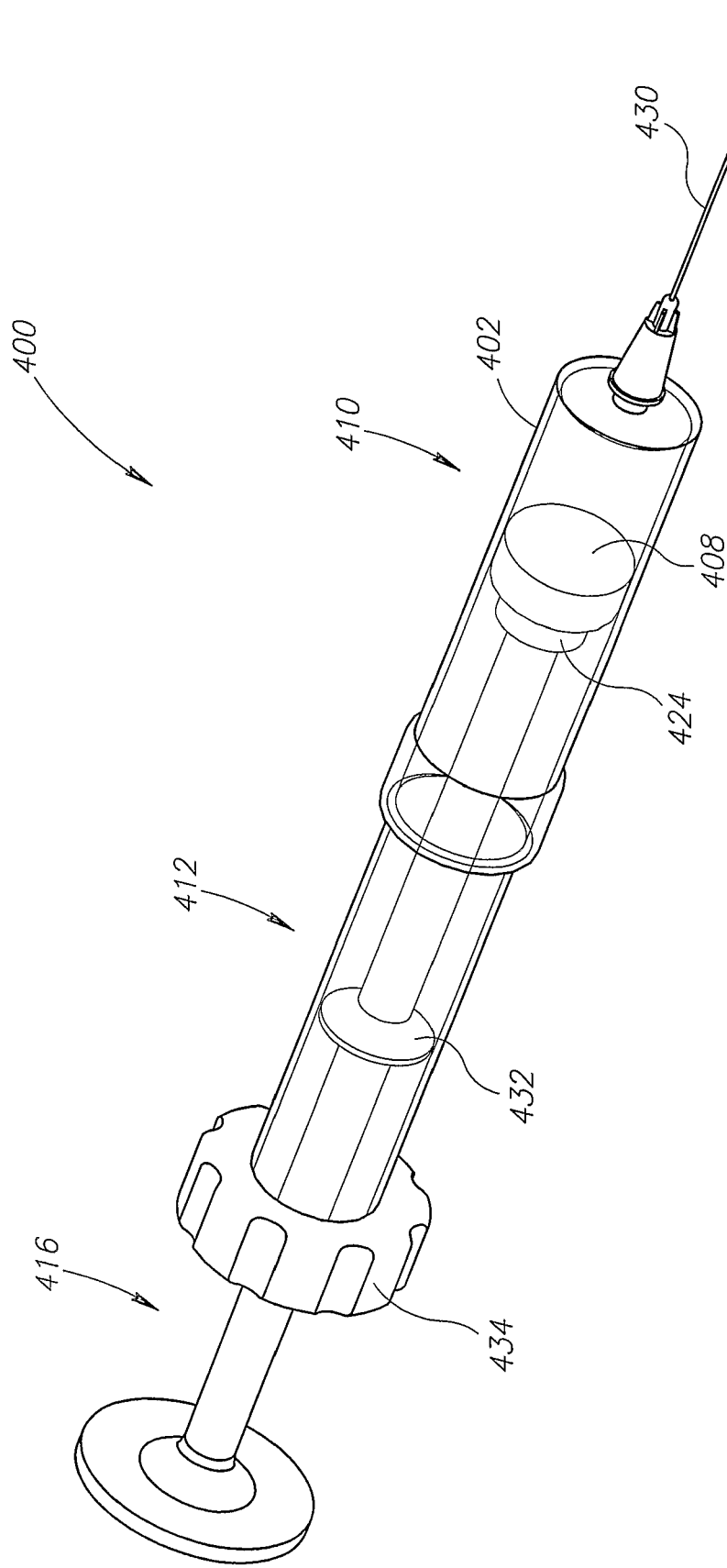
FIG. 18 is a perspective view of the syringe assembly of FIG. 18 in an assembled state.

Furthermore, this embodiment can be used for drawing blood samples for testing. Once plunger unit 412 and dispensing unit 410 are assembled to form syringe assembly 400 as illustrated in FIG. 18, plunger 416 is pushed into the syringe, moving plunger head 424, and bung 408 lockingly engaged thereto, to the top end of dispensing unit body 402. A hypodermic needle 430, which may be coupled to the syringe assembly 400, is inserted into a vein, and blood may flow into dispensing unit 410 via needle 430 when the plunger 416 is withdrawn. When bung 408 abuts against the top rim 428 of plunger unit body 414 (as shown in FIG. 17) and hermetically seals the bottom end of dispensing unit body 402, the dispensing unit may be safely removed from the plunger unit and a new dispensing unit may be coupled thereto for drawing a new sample of blood. It will be appreciated that as no part of the plunger unit 412 comes into contact with the blood, plunger unit 412 may be used repeatedly with any number of dispensing units. FIG. 18 further includes a stop member 432 which abuts against closure member 434 thus preventing accidental or unwanted removal of plunger 416 out of plunger unit 412.

According to yet another embodiment of the present invention, the plunger unit 412 as shown in FIGS. 17 and 18 can be coupled to an extension unit 311 and a dispensing unit 310 both as shown in FIGS. 14-16, to form a syringe assembly that can be used for separately storing two components, mixing and dispensing the solution formed, in one or several pre-set dosages. For that purpose, extension unit 311 is adapted and configured to disengage first extension bung 320 and lockingly coupled bung 364 from joining sleeve 319, allowing a two-way flow-communication between the compartment defined by body 316 of the extension unit and the compartment defined by body 102 of the dispensing unit, while at the same time, second extension bung 324 lockingly coupled to plunger head 132 maintains a sealing engagement with bottom end opening 322 of the extension unit, when plunger 340 is withdrawn. According to one embodiment, bung 324 is sized to keep opening 322 sealed longer than bung 320 can keep joining sleeve 319 sealed when sliding in tandem inside the syringe assembly upon withdrawing of the plunger. Preferably, bung 324 is longer than bung 320. Alternatively, connecting rod 326 may be sized to keep bung 324 away from bottom end opening 322 at a distance substantially equal to the distance necessary for bung 320 to slide out of joining sleeve 319 when plunger 340 is withdrawn, for allowing a flow-communication between the extension unit and the dispensing unit. It will be appreciated by one of ordinary skill in the art that the two-way flow-communication established between the extension unit and dispensing unit can be used to mix two components stored separately in these units and dispense the solution through the top end opening of the dispensing unit, or to allow a pre-set dosage of a component or solution stored in the extension unit to pass and fill the dispensing unit pre-sized to hold the dosage, and dispense the dosage. This procedure can be repeated until the component or solution is completely dispensed.

It will be appreciated that the relative diameters of the sidewalls of the plunger unit and the dispensing unit of this embodiment are such as to provide a barrier against sliding of the bung out of the dispensing unit. Alternatively, such a barrier can be provided in any other known manner. This barrier will prevent inadvertent leakage of contact between material in the dispensing unit and the plunger, and prevent contamination of the plunger unit, allowing the user to re-use the plunger unit without a need for cleaning or sterilization.

Most of the seals discussed herein in reference to the various embodiments of the multi-compartment syringe assembly are described as hermetic seals. However, the quality of the seals may be hermetic or non-hermetic as the particular application for the syringe assembly necessitates. The quality of the particular seal in the syringe assembly can be controlled by selecting appropriate materials for the components that form the seal. The particular physical arrangement or configuration of the components selected will also affect the quality of the seal. For example, in the embodiment of the syringe assembly where the top-end opening is sealed with a heat sealed membrane, the membrane may be selected from a variety of materials of having varying permeability with respect to air or the particular substance placed inside the dispensing unit to achieve the desired seal quality at the top-end opening.

It should be emphasized that the above described embodiments of the present invention are merely specific examples. In addition, components and formulations other than medicaments may be administered with the syringe. Various modifications may be made by those skilled in the art which will embody the principles of the invention and fall within the spirit and the scope thereof.

The invention claimed is:

1. A syringe assembly comprising:
   a dispensing unit including a substantially cylindrical dispensing unit body having top and bottom sealable open ends;
   a separate, independent plunger unit including a substantially cylindrical plunger unit body having a top open sealable end defining a joining sleeve, a bottom sealable open end, and an inner sidewall diameter that is larger than the diameter of said joining sleeve of said plunger unit body;
   said joining sleeve of said plunger unit body having an inner sidewall diameter which is substantially the same as an inner sidewall diameter of said dispensing unit body;
   a plunger disposed in the bottom open end of said plunger unit body, the plunger having a shaft and a plunger head;
   said plunger head having an outer diameter which is substantially the same as the inner sidewall diameter of said joining sleeve of said plunger unit body;
   wherein the bottom open end of said dispensing unit is adapted and configured for coaxial locking engagement with the top open opening of said plunger unit to form a multi-unit syringe assembly; and
   wherein said plunger head seals said plunger unit when it sealingly engages said joining sleeve of said plunger unit body, and allows two-way flow communication between said dispensing unit and said plunger unit when said plunger head is retracted into the plunger unit body and disengages from said joining sleeve of said plunger unit body.

2. The syringe assembly according to claim 1, wherein a lower portion of said dispensing unit defines a depending flange, said depending flange of said dispensing unit and said joining sleeve of said plunger unit body being adapted and configured for locking engagement with one another.

3. The syringe assembly according to claim 2, wherein said dispensing unit further comprises a sealing element disposed in an upper portion of said depending flange, for engagement by a top rim of said joining sleeve of said plunger unit body, to provide a hermetic seal between the dispensing unit and the plunger unit.

4. The syringe assembly according to claim 3, further comprising a seal for sealing the open bottom end of said dispensing unit.

5. The syringe assembly according to claim 4, wherein said seal of said bottom end of dispensing unit is a bung, said bung and said plunger head having a locking mechanism for releasably locking said bung to said plunger head, whereby said bung moves together with said plunger head in said syringe assembly.

6. The syringe assembly according to claim 1, wherein:
said dispensing unit further comprises a bung disposed in the sealable bottom opening of said dispensing unit; and
said plunger unit has an inner sidewall diameter smaller than the diameter said bung of said dispensing unit.

7. The syringe assembly according to claim 6, further comprising a locking mechanism for releasably locking said bung of said dispensing unit to said plunger head, whereby said plunger head and said lockingly engaged bung of said dispensing unit move together in said syringe assembly to dispense material from said dispensing unit.

8. The syringe assembly according to claim 1, further comprising a closure member for sealing the bottom end opening of said plunger unit, said closure member having a central aperture for receiving said plunger shaft.

9. The syringe assembly according to claim 1, and further comprising a locking mechanism for locking the plunger relative to said plunger unit body.

10. The syringe assembly according to claim 9, wherein said locking mechanism of said plunger shaft includes a pivotable screw arranged to seat in a step-shaped groove in the plunger shaft and selectably permit movement of the plunger, depending upon the depth to which it is screwed into the shaft.

11. The syringe assembly according to claim 1, wherein the top end opening of said dispensing unit body is sealed by a removable cover member.

12. A process for preparing a syringe assembly comprising:
(a) providing a dispensing unit having a dispensing unit body and a sealable opening at each of its top and bottom ends;
(b) providing a separate, independent plunger unit having a plunger unit body having:
a top open sealable end defining a joining sleeve, said joining sleeve having an inner sidewall diameter which is substantially the same as the inner sidewall diameter of said dispensing unit body;
a bottom sealable open end;
and an inner sidewall diameter that is larger than the diameter of said joining sleeve of said plunger unit body;
(c) placing a plunger within the plunger unit, the plunger having a shaft and a plunger head having an outer diameter which is substantially the same as the inner sidewall diameter of said joining sleeve of said plunger unit body; and
(d) coupling the dispensing unit coaxially to the plunger unit to form a two-unit syringe assembly;
wherein said plunger head seals said plunger unit when it sealingly engages said joining sleeve of said plunger unit body, and allows two-way flow communication between said dispensing unit and said plunger unit when said plunger head is retracted into the plunger unit body and disengages from said joining sleeve of said plunger unit body.

13. The process according to claim 12, further comprising the step of filling the dispensing unit before coupling said dispensing unit and said plunger unit to form the syringe assembly.

14. The process according to claim 12, further comprising the step of filling the dispensing unit and the plunger unit before coupling said dispensing unit and said plunger unit to form the syringe assembly.

15. The process according to claim 12, further comprising the step of filling the dispensing unit after coupling said dispensing unit and said plunger unit to form the syringe assembly.

16. A process for preparing a syringe assembly comprising:
(a) providing a dispensing unit having a housing and an opening at each of its top and bottom ends;
(b) sealing one end of the dispensing unit;
(c) introducing a first component of a formulation, if there is more than one, into the dispensing unit through the other end and sealing that end;
(d) providing a separate, independent plunger unit having a plunger unit body and a top open sealable end defining a joining sleeve having an inner sidewall diameter which is substantially the same as an inner sidewall diameter of said dispensing unit housing, a bottom sealable open end, and an inner sidewall diameter that is larger than the diameter of said joining sleeve of said plunger unit housing;
(e) placing a plunger within the plunger unit, the plunger having a plunger head adapted to form a seal closing the top opening of the plunger unit, the plunger head movable between a sealed position and an unsealed position, said unsealed position providing two-way flow communication between said plunger unit and said dispensing unit; the plunger being placed in the plunger unit in the sealed position;
(f) introducing a different component of the formulation, or a medicament if there is only one, into the plunger unit through the sealable filling opening of the plunger unit; and
(g) sealing the sealable filling opening,
so as to hold and store one or more components of a formulation separately until said units are assembled into a single multi-unit syringe for dispensing the formulation or for mixing the contents of the compartments prior to dispensing.

17. The process according to claim 12, wherein:
the step of providing a dispensing unit includes providing a dispensing unit including a bung disposed in the sealable bottom opening of said dispensing unit; and
the step of providing a plunger unit includes providing a plunger unit having an inner sidewall diameter smaller than said bung,
providing a locking mechanism for releasably locking said bung to said plunger head, whereby said plunger is enabled to push said bung to dispense material in said dispensing unit.

18. The process according to claim 16, wherein: the step of providing a dispensing unit includes providing a dispensing unit including a bung disposed in the sealable bottom opening of said dispensing unit; and the step of providing a plunger unit includes providing a plunger unit having an inner sidewall diameter smaller than said bung, providing a locking mechanism for releasably locking said bung to said plunger head, whereby said plunger is enabled to push said bung to dispense material in said dispensing unit.

* * * * *